United States Patent
Amrein et al.

(10) Patent No.: US 8,211,913 B2
(45) Date of Patent: *Jul. 3, 2012

(54) 5-ARYL PYRIDINES AS 11-BETA INHIBITORS FOR THE TREATMENT OF DIABETES

(75) Inventors: Kurt Amrein, Itingen (CH); Daniel Hunziker, Moehlin (CH); Bernd Kuhn, Liestal (CH); Alexander Mayweg, Loerrach (DE); Werner Neidhart, Hagenthal le Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 590 days.

This patent is subject to a terminal disclaimer.

(21) Appl. No.: 12/372,244

(22) Filed: Feb. 17, 2009

(65) Prior Publication Data

US 2009/0149503 A1    Jun. 11, 2009

Related U.S. Application Data

(62) Division of application No. 11/189,598, filed on Jul. 26, 2005, now Pat. No. 7,528,159.

(30) Foreign Application Priority Data

Jul. 28, 2004  (EP) .................................... 04103639

(51) Int. Cl.
*C07D 213/02* (2006.01)
*A61K 31/44* (2006.01)
(52) U.S. Cl. ......... 514/318; 546/193; 546/312; 514/352
(58) Field of Classification Search .................. None
See application file for complete search history.

(56) References Cited

U.S. PATENT DOCUMENTS
7,528,159 B2 * 5/2009 Amrein et al. ................ 514/352

OTHER PUBLICATIONS

Masuzaki H. et al., Science. Dec. 7, 2001; 294(5549):2166-70.
Walker et al. 1995; J. Clin. Endocrinol. Metab. 80, 31155-3159.
P.M. Stewart and Z.S. Krozowski, Vitam. Horm. 57 (1999), pp. 249-324.
Kotelevtsev Y. et al., Proc Natl Acad Sci U S A. Dec. 23, 1997;94(26):14924-9.
Masuzaki H. et al., J Clin Invest. Jul. 2003;112(1):83-90.
Rauz S. et al., QJM. Jul. 2003;96(7):481-90.
Sandeep TC. et al., Proc Natl Acad Sci U S A. Apr. 27, 2004;101(17):6734-9.

* cited by examiner

*Primary Examiner* — Zinna Northington Davis
(74) *Attorney, Agent, or Firm* — George W. Johnston; Dennis P. Tramaloni; Samuel H. Megerditchian

(57) ABSTRACT

Compounds of formula (I):

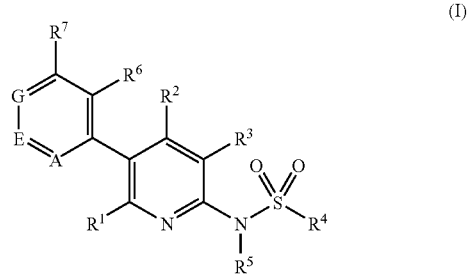

as well as pharmaceutically acceptable salts and esters thereof used in the form of pharmaceutical compositions.

21 Claims, No Drawings

5-ARYL PYRIDINES AS 11-BETA INHIBITORS FOR THE TREATMENT OF DIABETES

PRIORITY TO RELATED APPLICATION(S)

This application is a division of U.S. application Ser. No. 11/189,598, filed Jul. 26, 2005, now U.S. Pat. No. 7,528,159; which claims the benefit of European Application No. 04103639.3 filed Jul. 28, 2004. The entire contents of the above-identified applications are hereby incorporated by reference.

FIELD OF THE INVENTION

The present invention is directed to novel pyrimidine derivatives useful as 11b-HSD1 inhibitors (T2D).

The invention is concerned particularly with compounds of formula I

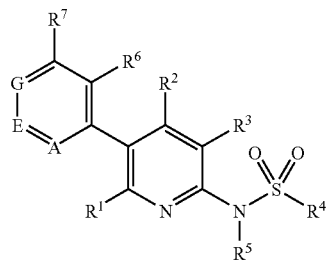

(I)

and pharmaceutically acceptable salts and esters thereof.

All documents cited or relied upon below are expressly incorporated herein by reference.

BACKGROUND OF THE INVENTION

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active forms. 11beta-hydroxysteroid dehydrogenases (11beta-HSD's) catalyze the interconversion of the principal active 11-hydroxy-glucocorticoid (cortisol) and their inactive 11-keto metabolites (cortisone).

The enzyme 11beta-hydroxysteroid dehydrogenase type 1 (11beta-HSD 1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD 1 in adipocytes of mice led to visceral obesity and to a syndrome-X like phenotype (Masuzaki H. et al., Science. 2001 Dec. 7; 294(5549):2166-70.). Taken together, the data very strongly supports an important role of 11beta-HSD 1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD 1 inhibition in humans might have beneficial effects were obtained by using carbenoxolone, an anti-ulcer drug which inhibits both 11beta-HSD 1 and the related enzyme 11beta-HSD2. Treatment with carbenoxolone led to an increase in insulin sensitivity indicating that that inhibition of 11beta-HSD 1 may reduce cellular cortisol levels and therefore minimizing some of its deleterious effects. (Walker et al. 1995; J. Clin. Endocrinol. Metab. 80, 31155-3159).

11beta-HSD 1 is expressed in many tissues including liver, adipose tissue, vascular smooth muscles, pancreas and brain. Its activity is dependent on NADP(H) and it has a relatively low affinity for its substrate (compared to 11beta-HSD2). 11 beta-HSD 1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplify glucocorticoid activity. It is this elevated cellular cortisol concentration that might lead to increased hepatic glucose production, adipocyte differentiation and insulin resistance.

Inhibition of 11beta-HSD 1 should not only reduce the typical Syndrome-X/Diabetes associated symptoms, but it should also be safe and without major side effect. Studies with the unspecific inhibitor carbenoxolone highlight the importance of developing specific 11beta-HSD 1 inhibitors. The inhibition of the 11beta-HSD2 enzyme is badly tolerated and results in increased blood pressure. In contrast inhibition of 11beta-HSD1 should be well tolerated since 11beta-HSD 1 knockout mice were found be healthy and to resist hyperglycemia provoked by obesity or stress (Kotelevtsev Y. et al., Proc Natl Acad Sci USA. 1997 Dec. 23; 94(26):14924-9). Similarly upon starvation these mice had attenuated activation of key hepatic enzymes that are involved in gluconeogenesis. In addition, these mice had improved lipid and lipoprotein profiles suggesting that inhibition of HSD 1 might be highly efficacious and safe. Recent reports indicate that 11beta-HSD 1 inhibitors might also be beneficial to reduce high blood pressure (Masuzaki H. et al., J Clin Invest. 2003 July; 112(1):83-90; Rauz S. et al., QJM. 2003 July; 96(7): 481-90) to improve cognition (Sandeep T C. et al., Proc Natl Acad Sci USA. 2004 Apr. 27; 101 (17):6734-9) or to improve Alzheimer associated deficits. A need exists in the art, therefore, for 11beta-HSD 1 inhibitors as a safe and efficacious approach to treat diabetes, obesity and other diseases.

SUMMARY OF THE INVENTION

In one embodiment of the present invention, provided is a compound of the formula (I):

wherein:
R¹ is hydrogen, alkyl, cycloalkyl, hydroxy, hydroxyalkyl, alkoxy, alkoxyalkyl, amino or aminoalkyl;
R² is hydrogen, alkyl or halogen;
R³ is hydrogen, alkyl or halogen;
R⁴ is phenyl, naphtyl, thiophenyl, pyridyl, quinolyl, piperidyl, morpholyl or thiomorpholyl optionally substituted with one or more substituents independently selected from alkyl, cycloalkyl, halogen, hydroxy, hydroxyalkyl, alkoxy, alkoxyalkyl, hydroxyalkoxy, alkoxyalkoxy, cyano, trifluoromethyl, trifluoromethoxy, aryl, arylalkyl, aryloxy, heterocyclyl, alkylcarbonylamino, alkoxycarbonylalkoxy and alkyl-SO₂—;
R⁵ is hydrogen or alkyl;
R⁶, R⁷, R⁸, R⁹ and R¹⁰ are independently selected from hydrogen, alkyl, halogen, cyano, trifluoromethyl, alkoxy and alkyl-SO₂—;
A is nitrogen or C—R¹⁰;
E is nitrogen or C—R⁹;
G is nitrogen or C—R⁸;
wherein not more than one of A, E and G is nitrogen;
and pharmaceutically acceptable salts and esters thereof.

In another embodiment of the invention, provided is a process for the preparation of a compound according to formula (I) comprising the step of reacting a compound according to formula (II):

in the presence of a compound according to formula wherein R¹ to R⁷, A, E and G are defined as in claim 1.

In a further embodiment of the invention, provided is a pharmaceutical composition comprising a therapeutically effective amount of a compound according to formula (I) and a therapeutically inert carrier.

In a still another embodiment of the present invention, provided is a method for the treatment and prophylaxis of diabetes, obesity, eating disorders, dyslipidemiae and hypertension, comprising the step of administering a therapeutically effective amount of a compound according to formula (I) to a patient in need thereof.

In a yet another embodiment of the invention, provided is a method for the treatment and prophylaxis of diabetes Type II, comprising the step of administering a therapeutically effective amount of a compound according to formula (I) to a patient in need thereof.

DETAILED DESCRIPTION

The compounds of formula I and their pharmaceutically acceptable salts and esters are novel and have valuable pharmacological properties. In particular, the compounds of formula I are 11b-HSD1 inhibitors (T2D) and display selectivity against the related 11beta-HSD2 enzyme. Therefore, the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II. The compounds of this invention can further be used in the prophylaxis and/or treatment of high ocular eye pressure, cognition, Alzheimer and/or neurodegeneration.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which The term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Preferred is phenyl or naphthyl, particularly phenyl optionally substituted with one to three, preferably one or two substituents independently selected from alkyl, halogen, alkoxy, trifluoromethoxy, nitro and trifluoromethyl. Particularly preferred is phenyl.

The term "aryloxy", alone or in combination, signifies a aryl-O— group in which the term "aryl" has the previously given significance.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred examples are thiophenyl, quinolyl, piperidyl, morpholyl, thiomorpholyl, oxazolyl, pyridinyl, pyrimidinyl, pyrazolyl, imidazolyl and thiazolyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "oxy", alone or in combination, signifies the —O— group.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Further preferred are compounds of formula I, wherein $R^1$ is hydrogen. Also preferred are compounds of formula I, wherein $R^1$ is alkyl, preferably methyl.

Another preferred object of the present invention are the compounds of formula I, wherein $R^2$ is hydrogen. Further preferred are those compounds according to formula I, wherein $R^2$ is alkyl.

Particularly preferred are those compounds of formula I, wherein $R^2$ is methyl.

Also preferred are the compounds of formula I, wherein $R^3$ is hydrogen. Further preferred are those compounds according to formula I, wherein $R^3$ is alkyl.

Another preferred aspect of the present invention are compounds of formula I, wherein $R^5$ is hydrogen.

Particularly preferred are those compounds of formula I, wherein A is C—$R^{10}$. Further preferred are those compounds of formula I, wherein A is nitrogen.

Preferred are those compounds of formula I, wherein E is C—$R^9$. Further preferred are those compounds of formula I, wherein E is nitrogen.

Another preferred aspect of the present invention are the compounds of formula I, wherein G is C—$R^8$. Also preferred are those compounds of formula I, wherein G is nitrogen.

Preferred are the compounds of formula I, wherein $R^4$ is phenyl, naphtyl, thiophenyl, pyridyl, quinolyl, piperidyl, morpholyl or thiomorpholyl optionally substituted with one to three, preferably one or two substituents independently selected from alkyl, cycloalkyl, halogen, hydroxy, hydroxyalkyl, alkoxy, alkoxyalkyl, hydroxyalkoxy, alkoxyalkoxy, cyano, trifluoromethyl, trifluoromethoxy, aryl, arylalkyl, aryloxy, heterocyclyl, alkylcarbonylamino, alkoxycarbonylalkoxy and alkyl-$SO_2$—.

Further preferred are compounds of formula I, wherein $R^4$ is phenyl optionally substituted with one to three substituents independently selected from alkyl, cycloalkyl, halogen, hydroxy, hydroxyalkyl, alkoxy, alkoxyalkyl, hydroxyalkoxy, alkoxyalkoxy, cyano, trifluoromethyl, trifluoromethoxy, aryl, arylalkyl, aryloxy, heterocyclyl, alkylcarbonylamino, alkoxycarbonylalkoxy and alkyl-$SO_2$—.

Particularly preferred are those compounds of formula I, wherein $R^4$ is phenyl substituted with one to three substituents independently selected from alkyl, halogen and trifluoromethyl.

Preferred are compounds of formula I, wherein $R^6$, $R^7$, $R^8$, $R^9$ and $R^{10}$ are independently selected from hydrogen, alkyl, halogen and trifluoromethyl.

Particularly preferred are those compounds of formula I, wherein $R^6$ is halogen, alkyl or trifluoromethyl. Especially preferred are those compounds of formula I, wherein $R^6$ is chloro, methyl or trifluoromethyl.

Examples of preferred compounds of formula (I) are:
N-[5-(2-Chloro-phenyl)-pyridin-2-yl]-5-fluoro-2-methyl-benzenesulfonamide;
3-Chloro-N-[5-(2-chloro-phenyl)-pyridin-2-yl]-2-methyl-benzenesulfonamide;
N-[5-(2,4-Dichloro-phenyl)-pyridin-2-yl]-5-fluoro-2-methyl-benzenesulfonamide;
4a) 3-Chloro-N-[5-(2,4-dichloro-phenyl)-pyridin-2-yl]-2-methyl-benzenesulfonamide;
4b) 3-Chloro-N-[5-(2-chloro-phenyl)-6-methyl-pyridin-2-yl]-2-methyl-benzenesulfonamide;
Biphenyl-4-sulfonic acid [5-(2-chloro-phenyl)-6-methyl-pyridin-2-yl]-amide;
3-Chloro-N-[5-(2-chloro-4-fluoro-phenyl)-pyridin-2-yl]-2-methyl-benzenesulfonamide;
3-Chloro-N-[5-(3-fluoro-phenyl)-pyridin-2-yl]-2-methyl-benzenesulfonamide;
3-Chloro-N-[5-(2,4-difluoro-phenyl)-pyridin-2-yl]-2-methyl-benzenesulfonamide;
N-[5-(2,4-Difluoro-phenyl)-pyridin-2-yl]-5-fluoro-2-methyl-benzenesulfonamide;
3-Chloro-N-[5-(4-methoxy-phenyl)-pyridin-2-yl]-2-methyl-benzenesulfonamide;
3-Chloro-N-[5-(4-fluoro-phenyl)-pyridin-2-yl]-2-methyl-benzenesulfonamide;
5-Fluoro-N-[5-(4-fluoro-phenyl)-pyridin-2-yl]-2-methyl-benzenesulfonamide;
5-Fluoro-N-[5-(2-methoxy-phenyl)-pyridin-2-yl]-2-methyl-benzenesulfonamide;
3-Chloro-N-[5-(2-fluoro-phenyl)-pyridin-2-yl]-2-methyl-benzenesulfonamide;
5-Fluoro-N-[5-(2-fluoro-phenyl)-pyridin-2-yl]-2-methyl-benzenesulfonamide;
2,4-Dichloro-N-[5-(2-chloro-phenyl)-pyridin-2-yl]-6-methyl-benzenesulfonamide;
N-[5-(2-Chloro-phenyl)-pyridin-2-yl]-2,5-difluoro-benzenesulfonamide;
3-Chloro-N-[5-(4-methanesulfonyl-phenyl)-pyridin-2-yl]-2-methyl-benzenesulfonamide;
3-Chloro-N-[5-(4-fluoro-phenyl)-6-methyl-pyridin-2-yl]-2-methyl-benzenesulfonamide;
5-Fluoro-N-[5-(4-fluoro-phenyl)-6-methyl-pyridin-2-yl]-2-methyl-benzenesulfonamide;
3-Chloro-N-[5-(3-fluoro-phenyl)-6-methyl-pyridin-2-yl]-2-methyl-benzenesulfonamide;
5-Fluoro-N-[5-(3-fluoro-phenyl)-6-methyl-pyridin-2-yl]-2-methyl-benzenesulfonamide;
N-[5-(2,4-Dichloro-phenyl)-pyridin-2-yl]-3,4-dimethoxy-benzenesulfonamide;
3,4-Dichloro-N-[5-(2,4-dichloro-phenyl)-pyridin-2-yl]-benzenesulfonamide;
N-[5-(2,3-Dichloro-phenyl)-pyridin-2-yl]-2,5-difluoro-benzenesulfonamide;
3-Chloro-N-[5-(2,3-dichloro-phenyl)-pyridin-2-yl]-2-methyl-benzenesulfonamide;
3,4-Dichloro-N-[5-(2-chloro-phenyl)-pyridin-2-yl]-benzenesulfonamide;
N-[5-(2-Chloro-phenyl)-pyridin-2-yl]-3,4-dimethoxy-benzenesulfonamide;
3-Chloro-N-[5-(2-chloro-phenyl)-pyridin-2-yl]-4-methyl-benzenesulfonamide;
5-Fluoro-N-[5-(4-fluoro-2-methyl-phenyl)-pyridin-2-yl]-2-methyl-benzenesulfonamide;
3-Chloro-N-[5-(4-fluoro-2-methyl-phenyl)-pyridin-2-yl]-2-methyl-benzenesulfonamide;
3-Chloro-N-[5-(2-chloro-phenyl)-pyridin-2-yl]-4-methoxy-benzenesulfonamide;
4,5-Dichloro-N-[5-(2-chloro-phenyl)-pyridin-2-yl]-2-fluoro-benzenesulfonamide;
3-Chloro-N-[5-(2,4-dichloro-phenyl)-pyridin-2-yl]-4-methoxy-benzenesulfonamide;
3-Chloro-N-[5-(2,4-dichloro-phenyl)-pyridin-2-yl]-4-methyl-benzenesulfonamide;
Piperidine-1-sulfonic acid [5-(2,4-dichloro-phenyl)-pyridin-2-yl]-amide;
N-[5-(2,3-Dichloro-phenyl)-pyridin-2-yl]-2-trifluoromethyl-benzenesulfonamide;
N-[5-(2,3-Dichloro-phenyl)-pyridin-2-yl]-4-fluoro-benzenesulfonamide;
N-[5-(2,5-Dichloro-phenyl)-pyridin-2-yl]-2,5-difluoro-benzenesulfonamide;
N-[5-(2,5-Dichloro-phenyl)-pyridin-2-yl]-5-fluoro-2-methyl-benzenesulfonamide;
3-Chloro-N-[5-(2,5-dichloro-phenyl)-pyridin-2-yl]-2-methyl-benzenesulfonamide;
5-Fluoro-N-[5-(2-fluoro-5-trifluoromethyl-phenyl)-pyridin-2-yl]-2-methyl-benzenesulfonamide;
3-Chloro-N-[5-(2-fluoro-5-trifluoromethyl-phenyl)-pyridin-2-yl]-2-methyl-benzenesulfonamide;
3-Chloro-2-methyl-N-[5-(2-trifluoromethyl-phenyl)-pyridin-2-yl]-benzenesulfonamide;
3-Chloro-4-methyl-N-[5-(2-trifluoromethyl-phenyl)-pyridin-2-yl]-benzenesulfonamide;
5-Chloro-N-[5-(2,4-dichloro-phenyl)-pyridin-2-yl]-2-methoxy-benzenesulfonamide;
N-{2-Chloro-4-[5-(2,4-dichloro-phenyl)-pyridin-2-ylsulfamoyl]-phenyl}-acetamide;
N-[5-(2,4-Dichloro-phenyl)-pyridin-2-yl]-4-trifluoromethyl-benzenesulfonamide;
N-[5-(2,4-Dichloro-phenyl)-pyridin-2-yl]-4-methylsulfonyl-benzenesulfonamide;
3-Chloro-N-[5-(2,3-difluoro-phenyl)-pyridin-2-yl]-4-methyl-benzenesulfonamide;
N-[5-(2,3-Difluoro-phenyl)-pyridin-2-yl]-5-fluoro-2-methyl-benzenesulfonamide;
N-[5-(2,4-Bis-trifluoromethyl-phenyl)-pyridin-2-yl]-3-chloro-2-methyl-benzenesulfonamide;

N-[5-(2,4-Bis-trifluoromethyl-phenyl)-pyridin-2-yl]-3-chloro-4-methyl-benzenesulfonamide;
3-Chloro-N-[5-(2,3-difluoro-phenyl)-pyridin-2-yl]-2-methyl-benzenesulfonamide;
Piperidine-1-sulfonic acid [5-(2,3-dichloro-phenyl)-pyridin-2-yl]-amide;
5-Chloro-N-[5-(4-fluoro-phenyl)-6-methyl-pyridin-2-yl]-2-methoxy-benzenesulfonamide;
N-{2-Chloro-4-[5-(4-fluoro-phenyl)-6-methyl-pyridin-2-ylsulfamoyl]-phenyl}-acetamide;
N-[5-(4-Fluoro-phenyl)-6-methyl-pyridin-2-yl]-4-trifluoromethyl-benzenesulfonamide;
N-[5-(4-Fluoro-phenyl)-6-methyl-pyridin-2-yl]-4-methanesulfonyl-benzenesulfonamide;
{4-[5-(2,3-Dichloro-phenyl)-pyridin-2-ylsulfamoyl]-phenoxy}-acetic acid methyl ester;
N-[5-(4-Fluoro-phenyl)-6-methyl-pyridin-2-yl]-4-trifluoromethoxy-benzenesulfonamide;
3-Chloro-N-[5-(4-fluoro-phenyl)-6-methyl-pyridin-2-yl]-4-methoxy-benzenesulfonamide;
4-Chloro-N-[5-(4-fluoro-phenyl)-6-methyl-pyridin-2-yl]-2,5-dimethyl-benzenesulfonamide;
N-[5-(2,3-Dichloro-phenyl)-pyridin-2-yl]-4-(2-hydroxy-ethoxy)-benzenesulfonamide;
N-[5-(2-Chloro-phenyl)-6-methyl-pyridin-2-yl]-4-fluoro-benzenesulfonamide;
3-Chloro-N-[5-(2-chloro-phenyl)-6-methyl-pyridin-2-yl]-4-methyl-benzenesulfonamide;
4-Chloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-6-methyl-benzenesulfonamide;
Piperidine-1-sulfonic acid [5-(2-chloro-phenyl)-6-methyl-pyridin-2-yl]-amide;
N-[5-(2,4-Dichloro-phenyl)-pyridin-2-yl]-4-fluoro-benzenesulfonamide;
4-Chloro-N-[5-(2,4-dichloro-phenyl)-pyridin-2-yl]-2,5-dimethyl-benzenesulfonamide;
N-[5-(2,4-Dichloro-phenyl)-pyridin-2-yl]-2,4-difluoro-benzenesulfonamide;
2,4-Dichloro-N-[5-(2,4-dichloro-phenyl)-pyridin-2-yl]-5-methyl-benzenesulfonamide;
N-[5-(2,3-Dichloro-phenyl)-pyridin-2-yl]-3-trifluoromethyl-benzenesulfonamide
4-Fluoro-N-[5-(4-fluoro-2-methyl-phenyl)-6-methyl-pyridin-2-yl]-benzenesulfonamide;
3-Chloro-N-[5-(4-fluoro-2-methyl-phenyl)-6-methyl-pyridin-2-yl]-2-methyl-benzenesulfonamide;
5-Fluoro-N-[5-(4-fluoro-2-methyl-phenyl)-6-methyl-pyridin-2-yl]-2-methyl-benzenesulfonamide;
3-Chloro-N-[5-(2,3-dichloro-phenyl)-pyridin-2-yl]-4-methyl-benzenesulfonamide;
N-[5-(2,3-Dichloro-phenyl)-pyridin-2-yl]-4-trifluoromethyl-benzenesulfonamide;
3-Chloro-N-[5-(4-fluoro-2-methyl-phenyl)-pyridin-2-yl]-4-methyl-benzenesulfonamide;
N-[5-(4-Fluoro-2-methyl-phenyl)-pyridin-2-yl]-3-trifluoromethyl-benzenesulfonamide;
N-[5-(4-Fluoro-2-methyl-phenyl)-pyridin-2-yl]-4-trifluoromethyl-benzenesulfonamide;
N-[5-(2-Chloro-phenyl)-pyridin-2-yl]-3-trifluoromethyl-benzenesulfonamide;
N-[5-(2-Chloro-phenyl)-pyridin-2-yl]-4-ethyl-benzenesulfonamide;
3-Chloro-N-[5-(2-chloro-phenyl)-pyridin-2-yl]-benzenesulfonamide;
3-Chloro-N-[5-(2,4-dichloro-phenyl)-pyridin-2-yl]-4-fluoro-benzenesulfonamide;
N-[5-(2,4-Dichloro-phenyl)-pyridin-2-yl]-4-ethyl-benzenesulfonamide;
N-[5-(2,4-Dichloro-phenyl)-pyridin-2-yl]-3-trifluoromethyl-benzenesulfonamide;
N-[5-(2-Chloro-phenyl)-6-methyl-pyridin-2-yl]-3-trifluoromethyl-benzenesulfonamide;
N-[5-(2-Chloro-phenyl)-6-methyl-pyridin-2-yl]-4-trifluoromethoxy-benzenesulfonamide;
N-[5-(2-Chloro-phenyl)-pyridin-2-yl]-4-fluoro-benzenesulfonamide;
N-[5-(2-Chloro-phenyl)-pyridin-2-yl]-2,4-difluoro-benzenesulfonamide;
4-Chloro-N-[5-(2-chloro-phenyl)-pyridin-2-yl]-2,5-dimethyl-benzenesulfonamide;
4-Chloro-N-[5-(2-chloro-phenyl)-6-methyl-pyridin-2-yl]-2,5-dimethyl-benzenesulfonamide;
N-[5-(2-Chloro-phenyl)-6-methyl-pyridin-2-yl]-2,4-difluoro-benzenesulfonamide;
3,5-Dichloro-N-[5-(2-chloro-phenyl)-6-methyl-pyridin-2-yl]-benzenesulfonamide;
N-[5-(2,4-Dichloro-phenyl)-6-methyl-pyridin-2-yl]-3-trifluoromethyl-benzenesulfonamide;
N-[5-(2,4-Dichloro-phenyl)-6-methyl-pyridin-2-yl]-4-fluoro-benzenesulfonamide;
N-[5-(2,4-Dichloro-phenyl)-6-methyl-pyridin-2-yl]-2,4-difluoro-benzenesulfonamide;
4-Chloro-N-[5-(2,4-dichloro-phenyl)-6-methyl-pyridin-2-yl]-2,5-dimethyl-benzenesulfonamide;
2,4-Dichloro-N-[5-(2,4-dichloro-phenyl)-pyridin-2-yl]-6-methyl-benzenesulfonamide;
3-Chloro-N-[5-(2,4-dichloro-phenyl)-pyridin-2-yl]-benzenesulfonamide;
4-Chloro-N [5-(2,4-dichloro-phenyl)-pyridin-2-yl]-benzenesulfonamide;
N-[5-(2-Chloro-phenyl)-6-methyl-pyridin-2-yl]-3-fluoro-benzenesulfonamide;
3-Chloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-5-methyl-benzenesulfonamide;
N-[5-(4-Fluoro-2-methyl-phenyl)-6-methyl-pyridin-2-yl]-3-trifluoromethyl-benzenesulfonamide;
2,4-Dichloro-N-[5-(4-fluoro-2-methyl-phenyl)-6-methyl-pyridin-2-yl]-6-methyl-benzenesulfonamide;
3-Chloro-N-[5-(4-fluoro-2-methyl-phenyl)-6-methyl-pyridin-2-yl]-benzenesulfonamide;
4-Chloro-N-[5-(4-fluoro-2-methyl-phenyl)-6-methyl-pyridin-2-yl]-benzenesulfonamide;
N-[5-(4-Fluoro-2-methyl-phenyl)-6-methyl-pyridin-2-yl]-4-trifluoromethoxy-benzenesulfonamide;
N-[5-(4-Fluoro-2-methyl-phenyl)-6-methyl-pyridin-2-yl]-3-methyl-benzenesulfonamide;
2-Chloro-N-[5-(4-fluoro-2-methyl-phenyl)-6-methyl-pyridin-2-yl]-5-trifluoromethyl-benzenesulfonamide;
4-Fluoro-N-[5-(4-fluoro-2-methyl-phenyl)-6-methyl-pyridin-2-yl]-3-trifluoromethyl-benzenesulfonamide;
N-[5-(2-Chloro-phenyl)-6-methyl-pyridin-2-yl]-3-methyl-benzenesulfonamide;
3-Chloro-N-(2-chloro-phenyl)-6-methyl-pyridin-2-yl]-4-fluoro-benzenesulfonamide;
2-Chloro-N-[5-(2-chloro-phenyl)-6-methyl-pyridin-2-yl]-5-trifluoromethyl-benzenesulfonamide;

N-[5-(2-Chloro-phenyl)-6-methyl-pyridin-2-yl]-4-fluoro-3-trifluoromethyl-benzenesulfonamide;
N-[5-(2,3-Dichloro-phenyl)-pyridin-2-yl]-3-fluoro-4-methyl-benzenesulfonamide;
N-[5-(2,3-Dichloro-phenyl)-pyridin-2-yl]-3,5-dimethyl-benzenesulfonamide;
N-[5-(5-Fluoro-2-methyl-phenyl)-pyridin-2-yl]-3-trifluoromethyl-benzenesulfonamide;
4-Fluoro-N-[5-(5-fluoro-2-methyl-phenyl)-pyridin-2-yl]-benzenesulfonamide;
3-Chloro-N-[5-(5-fluoro-2-methyl-phenyl)-pyridin-2-yl]-2-methyl-benzenesulfonamide;
N-[5-(5-Chloro-2-methyl-phenyl)-pyridin-2-yl]-3-trifluoromethyl-benzenesulfonamide;
N-[5-(5-Chloro-2-methyl-phenyl)-pyridin-2-yl]-4-fluoro-benzenesulfonamide;
3-Chloro-N-[5-(5-chloro-2-methyl-phenyl)-pyridin-2-yl]-2-methyl-benzenesulfonamide;
3-Chloro-N-[5-(6-chloro-2-fluoro-3-methyl-phenyl)-pyridin-2-yl]-2-methyl-benzenesulfonamide;
N-[5-(6-Chloro-2-fluoro-3-methyl-phenyl)-pyridin-2-yl]-3-trifluoromethyl-benzenesulfonamide;
N-[5-(6-Chloro-2-fluoro-3-methyl-phenyl)-pyridin-2-yl]-4-fluoro-benzenesulfonamide;
N-[5-(5-Chloro-2-methyl-phenyl)-6-methyl-pyridin-2-yl]-3-trifluoromethyl-benzenesulfonamide;
N-[5-(5-Chloro-2-methyl-phenyl)-6-methyl-pyridin-2-yl]-4-fluoro-benzenesulfonamide;
3-Chloro-N-[5-(5-chloro-2-methyl-phenyl)-6-methyl-pyridin-2-yl]-2-methyl-benzenesulfonamide;
N-[5-(6-Chloro-2-fluoro-3-methyl-phenyl)-6-methyl-pyridin-2-yl]-3-trifluoromethyl-benzenesulfonamide;
N-[5-(6-Chloro-2-fluoro-3-methyl-phenyl)-6-methyl-pyridin-2-yl]-4-fluoro-benzenesulfonamide;
4-Chloro-N-[5-(4-fluoro-2-methyl-phenyl)-pyridin-2-yl]-benzenesulfonamide;
3-Chloro-N-[5-(4-fluoro-2-methyl-phenyl)-pyridin-2-yl]-benzenesulfonamide;
2,4-Dichloro-N-[5-(4-fluoro-2-methyl-phenyl)-pyridin-2-yl]-6-methyl-benzenesulfonamide;
3-Chloro-N-[5-(2,5-dichloro-phenyl)-6-methyl-pyridin-2-yl]-benzenesulfonamide;
N-[5-(2,5-Dichloro-phenyl)-6-methyl-pyridin-2-yl]-4-fluoro-benzenesulfonamide;
N-[5-(5-Fluoro-2-methyl-phenyl)-6-methyl-pyridin-2-yl]-3-trifluoromethyl-benzenesulfonamide;
4-Fluoro-N-[5-(5-fluoro-2-methyl-phenyl)-6-methyl-pyridin-2-yl]-benzenesulfonamide;
3-Chloro-N-[5-(5-fluoro-2-methyl-phenyl)-6-methyl-pyridin-2-yl]-benzenesulfonamide;
N-[5-(2,5-Dichloro-phenyl)-6-methyl-pyridin-2-yl]-3-trifluoromethyl-benzenesulfonamide;
N-[5-(2-Chloro-4-fluoro-phenyl)-6-methyl-pyridin-2-yl]-3-trifluoromethyl-benzenesulfonamide;
N-[5-(2-Chloro-4-fluoro-phenyl)-6-methyl-pyridin-2-yl]-4-fluoro-benzenesulfonamide;
3-Chloro-N-[5-(2-chloro-4-fluoro-phenyl)-6-methyl-pyridin-2-yl]-benzenesulfonamide;
N-[5-(2,3-Dichloro-phenyl)-6-methyl-pyridin-2-yl]-3-trifluoromethyl-benzenesulfonamide;
N-[5-(2,3-Dichloro-phenyl)-6-methyl-pyridin-2-yl]-4-fluoro-benzenesulfonamide;
3-Chloro-N-[5-(2,3-dichloro-phenyl)-6-methyl-pyridin-2-yl]-benzenesulfonamide;
2,4-Dichloro-N-[5-(2,3-dichloro-phenyl)-6-methyl-pyridin-2-yl]-6-methyl-benzenesulfonamide;
N-[5-(2,3-Dichloro-phenyl)-6-methyl-pyridin-2-yl]-3-methyl-benzenesulfonamide;
2,4-Dichloro-N-[5-(2,5-dichloro-phenyl)-6-methyl-pyridin-2-yl]-6-methyl-benzenesulfonamide;
N-[5-(2-Chloro-4-fluoro-phenyl)-6-methyl-pyridin-2-yl]-3-methyl-benzenesulfonamide;
2,4-Dichloro-N-[5-(2-chloro-4-fluoro-phenyl)-6-methyl-pyridin-2-yl]-6-methyl-benzenesulfonamide;
N-[5-(2,4-Bis-trifluoromethyl-phenyl)-pyridin-2-yl]-3-chloro-benzenesulfonamide;
N-[5-(2,4-Bis-trifluoromethyl-phenyl)-pyridin-2-yl]-3-methyl-benzenesulfonamide;
N-[5-(2,4-Bis-trifluoromethyl-phenyl)-pyridin-2-yl]-4-fluoro-benzenesulfonamide;
N-[5-(2,3-Dichloro-phenyl)-6-methyl-pyridin-2-yl]-4-fluoro-3-trifluoromethyl-benzenesulfonamide;
3-Chloro-N-[5-(2,3-dichloro-phenyl)-6-methyl-pyridin-2-yl]-4-fluoro-benzenesulfonamide;
3-Chloro-N-[5-(2-fluoro-phenyl)-6-methyl-pyridin-2-yl]-benzenesulfonamide;
4-Fluoro-N-[5-(2-fluoro-phenyl)-6-methyl-pyridin-2-yl]-benzenesulfonamide;
4-Fluoro-N-[5-(2-fluoro-phenyl)-6-methyl-pyridin-2-yl]-3-trifluoromethyl-benzenesulfonamide;
N-[5-(2,4-Bis-trifluoromethyl-phenyl)-pyridin-2-yl]-3-chloro-4-fluoro-benzenesulfonamide;
2,4-Dichloro-N-[5-(2-fluoro-phenyl)-6-methyl-pyridin-2-yl]-6-methyl-benzenesulfonamide;
N-[5-(2-Fluoro-phenyl)-6-methyl-pyridin-2-yl]-3-trifluoromethyl-benzenesulfonamide;
N-[5-(2-Chloro-phenyl)-3,4-dimethyl-pyridin-2-yl]-3-trifluoromethyl-benzenesulfonamide;
3-Chloro-N-[5-(2-chloro-phenyl)-3,4-dimethyl-pyridin-2-yl]-benzenesulfonamide;
N-[5-(2-Chloro-phenyl)-3,4-dimethyl-pyridin-2-yl]-4-fluoro-benzenesulfonamide;
N-(2-Methyl-[3,3']bipyridinyl-6-yl)-3-trifluoromethyl-benzenesulfonamide;
3-Chloro-N-[5-(2-chloro-phenyl)-4-methyl-pyridin-2-yl]-benzenesulfonamide;
N-[5-(2-Chloro-phenyl)-4-methyl-pyridin-2-yl]-3-trifluoromethyl-benzenesulfonamide;
2,4-Dichloro-N-[5-(2-chloro-phenyl)-4-methyl-pyridin-2-yl]-6-methyl-benzenesulfonamide;
3-Chloro-N-(2-methyl-[3,3']bipyridinyl-6-yl)-benzenesulfonamide;
3-Chloro-N-[5-(4-fluoro-2-methyl-phenyl)-4-methyl-pyridin-2-yl]-benzenesulfonamide;
N-[5-(4-Fluoro-2-methyl-phenyl)-4-methyl-pyridin-2-yl]-3-trifluoromethyl-benzenesulfonamide; and
2,4-Dichloro-N-[5-(4-fluoro-2-methyl-phenyl)-4-methyl-pyridin-2-yl]-6-methyl-benzenesulfonamide.

Examples of particularly preferred compounds of formula (I) are:
N-[5-(2-Chloro-phenyl)-pyridin-2-yl]-5-fluoro-2-methyl-benzenesulfonamide;
3-Chloro-N-[5-(2-chloro-phenyl)-pyridin-2-yl]-2-methyl-benzenesulfonamide;
3-Chloro-N-[5-(2,4-dichloro-phenyl)-pyridin-2-yl]-2-methyl-benzenesulfonamide;
3-Chloro-N-[5-(2-chloro-phenyl)-6-methyl-pyridin-2-yl]-2-methyl-benzenesulfonamide;
4,5-Dichloro-N-[5-(2-chloro-phenyl)-pyridin-2-yl]-2-fluoro-benzenesulfonamide;
3-Chloro-N-[5-(2,4-dichloro-phenyl)-pyridin-2-yl]-4-methyl-benzenesulfonamide;

Piperidine-1-sulfonic acid [5-(2,4-dichloro-phenyl)-pyridin-2-yl]-amide;
N-[5-(2,3-Dichloro-phenyl)-pyridin-2-yl]-4-fluoro-benzenesulfonamide;
3-Chloro-N-[5-(2-chloro-phenyl)-6-methyl-pyridin-2-yl]-4-methyl-benzenesulfonamide;
4-Chloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-6-methyl-benzenesulfonamide;
N-[5-(2,4-Dichloro-phenyl)-pyridin-2-yl]-4-fluoro-benzenesulfonamide;
N-[5-(2,4-Dichloro-phenyl)-pyridin-2-yl]-2,4-difluoro-benzenesulfonamide;
3-Chloro-N-[5-(4-fluoro-2-methyl-phenyl)-6-methyl-pyridin-2-yl]-2-methyl-benzenesulfonamide;
3-Chloro-N-[5-(2,3-dichloro-phenyl)-pyridin-2-yl]-4-methyl-benzenesulfonamide;
3-Chloro-N-[5-(4-fluoro-2-methyl-phenyl)-pyridin-2-yl]-4-methyl-benzenesulfonamide;
N-[5-(4-Fluoro-2-methyl-phenyl)-pyridin-2-yl]-3-trifluoromethyl-benzenesulfonamide;
N-[5-(2,4-Dichloro-phenyl)-pyridin-2-yl]-3-trifluoromethyl-benzenesulfonamide;
N-[5-(2-Chloro-phenyl)-6-methyl-pyridin-2-yl]-3-trifluoromethyl-benzenesulfonamide;
N-[5-(2-Chloro-phenyl)-pyridin-2-yl]-4-fluoro-benzenesulfonamide;
N-[5-(2-Chloro-phenyl)-6-methyl-pyridin-2-yl]-2,4-difluoro-benzenesulfonamide;
N-[5-(2,4-Dichloro-phenyl)-6-methyl-pyridin-2-yl]-2,4-difluoro-benzenesulfonamide;
2,4-Dichloro-N-[5-(2,4-dichloro-phenyl)-pyridin-2-yl]-6-methyl-benzenesulfonamide;
2,4-Dichloro-N-[5-(2-chloro-phenyl)-6-methyl-pyridin-2-yl]-benzenesulfonamide;
N-[5-(4-Fluoro-2-methyl-phenyl)-6-methyl-pyridin-2-yl]-3-trifluoromethyl-benzenesulfonamide;
3-Chloro-N-[5-(4-fluoro-2-methyl-phenyl)-6-methyl-pyridin-2-yl]-benzenesulfonamide;
N-[5-(4-Fluoro-2-methyl-phenyl)-6-methyl-pyridin-2-yl]-3-methyl-benzenesulfonamide;
N-[5-(5-Fluoro-2-methyl-phenyl)-pyridin-2-yl]-3-trifluoromethyl-benzenesulfonamide;
N-[5-(5-Chloro-2-methyl-phenyl)-pyridin-2-yl]-3-trifluoromethyl-benzenesulfonamide;
N-[5-(6-Chloro-2-fluoro-3-methyl-phenyl)-pyridin-2-yl]-4-fluoro-benzenesulfonamide;
3-Chloro-N-[5-(4-fluoro-2-methyl-phenyl)-pyridin-2-yl]-benzenesulfonamide;
2,4-Dichloro-N-[5-(4-fluoro-2-methyl-phenyl)-pyridin-2-yl]-6-methyl-benzenesulfonamide;
4-Fluoro-N-[5-(5-fluoro-2-methyl-phenyl)-6-methyl-pyridin-2-yl]-benzenesulfonamide;
N-[5-(2-Chloro-4-fluoro-phenyl)-6-methyl-pyridin-2-yl]-3-trifluoromethyl-benzenesulfonamide;
2,4-Dichloro-N-[5-(2,3-dichloro-phenyl)-6-methyl-pyridin-2-yl]-6-methyl-benzenesulfonamide;
2,4-Dichloro-N-[5-(2-chloro-4-fluoro-phenyl)-6-methyl-pyridin-2-yl]-6-methyl-benzenesulfonamide;
N-[5-(2,4-Bis-trifluoromethyl-phenyl)-pyridin-2-yl]-3-chloro-benzenesulfonamide;
3-Chloro-N-[5-(2-chloro-phenyl)-4-methyl-pyridin-2-yl]-benzenesulfonamide;
N-[5-(2-Chloro-phenyl)-4-methyl-pyridin-2-yl]-3-trifluoromethyl-benzenesulfonamide;
3-Chloro-N-[5-(4-fluoro-2-methyl-phenyl)-4-methyl-pyridin-2-yl]-benzenesulfonamide;
N-[5-(4-Fluoro-2-methyl-phenyl)-4-methyl-pyridin-2-yl]-3-trifluoromethyl-benzenesulfonamide; and
2,4-Dichloro-N-[5-(4-fluoro-2-methyl-phenyl)-4-methyl-pyridin-2-yl]-6-methyl-benzenesulfonamide.

Processes for the manufacture of compounds of formula I are an object of the invention.

The preparation of compounds of formula I of the present invention may be carried out in sequential or convergent synthetic routes. Syntheses of the invention are shown in the following Schemes. The skills required for carrying out the reaction and purification of the resulting products are known to those in the art. The substituents and indices used in the following description of the processes have the significance given above unless indicated to the contrary.

Compounds of general formula I can be obtained according to scheme 1 from compounds of formula II comprising $R^1$ to $R^7$ substituents and A, E, G definitions according to the above description via a condensation reaction with aryl, heteroaryl or heterocyclyl sulfonyl chlorides, in the presence of a base such as trietylamine or (4-dimethylamino)-pyridine (DMAP) in a solvent such THF, ethanol, methylene chloride DMF or DMSO, or in pyridine as a solvent, with or without the addition of a base such as trietylamine or DMAP, at room temperature or at elevated temperatures, to give compounds of general formula I. Compounds of formula I where $R^5$ equals alkyl can also be prepared from compounds of formula I where R5 equals H via an alkylation reaction, using, for example, NaH as a base and DMF as solvent, at room temperature or at elevated temperatures.

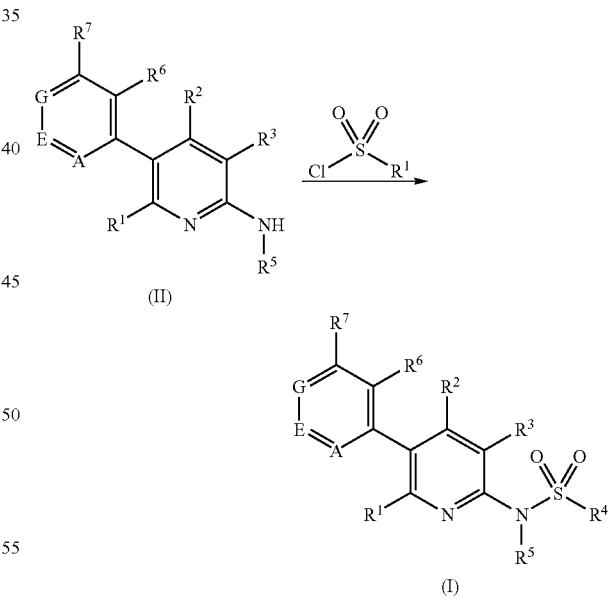

Scheme 1

Alternatively, compound of general formula I can be prepared according to scheme 2 from compounds of general formula III in a substitution reaction with an corresponding aryl heteroaryl or heterocyclyl sulphonamide, in the presence of a base such as sodium hydride, $Na_2CO_3$ or triethyl amine and in a solvent such as THF, DMF or DMSO at room temperature or at elevated temperatures. The reaction can also be carried out under the condition of an Ullman-type reaction with, for example Cu(I) chloride, or Cu(I) iodide in a solvent such as dioxane or DMF, in analogy to a method described by S. L. Buchwald (J. Am. Chem. Soc., 2001, 7727).

Scheme 2

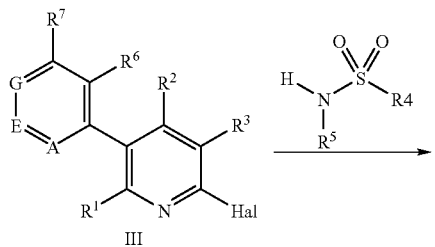

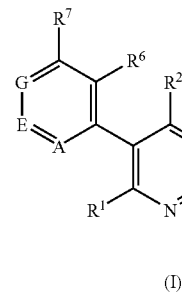

A further alternative consists of reacting compounds of general formula IV via a metal-catalysed (Pd or Ni) cross-coupling reaction with corresponding organometallic reagent such as (hetero)arylboron, (hetero)arylzink or (hetero)aryltin reagents using Suzuki-, Stille- or Negishi-type coupling reactions (for literature: Suzuki, Chem. Rev., 1995, 95, 2475; Stille, Angew. Chem. IEE, 1986, 25, 508; Negishi, Acc. Chem. Res., 1982, 15, 340).

Scheme 3

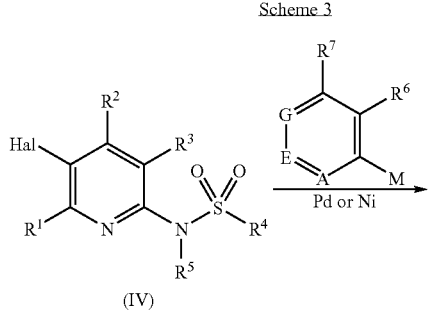

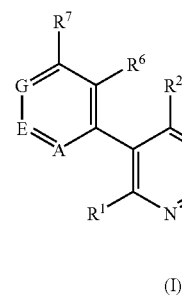

M: B(OH)$_2$, SnR$_3$ or ZnBr

Intermediated II, III and IV are either commercial available, known in the literature or can be prepared by applying a sequence of standard reactions known in the art and outlined in scheme 4. Thus, starting from appropriate 2-pyridones of formula V, which are either known in the literature or can be prepared according to standard procedures, subsequent halogenation with POCl$_3$, PCl$_3$ or POBr$_3$ gives rise to the corresponding 2-chloro or 2-bromo pyridines of formula VI. The iodo derivatives can be obtained from the chloro or bromo derivatives via halogen exchange with NaI (for general reaction of this type: R. C. Corcoran, Tetrahedron Lett. 1990, p 6757). Subsequent reaction with alkyl amines or ammonia, either applied in access, without solvent, or in equimolar amounts, in a suited solvent such as ethanol, water, DMF or THF, gives rise to compounds of formula VII. The reaction can also be performed in an autoclave at elevated pressure in analogy to published procedures (for an example: T. Haga, Heterocycles, 22, p 117).

Scheme 4

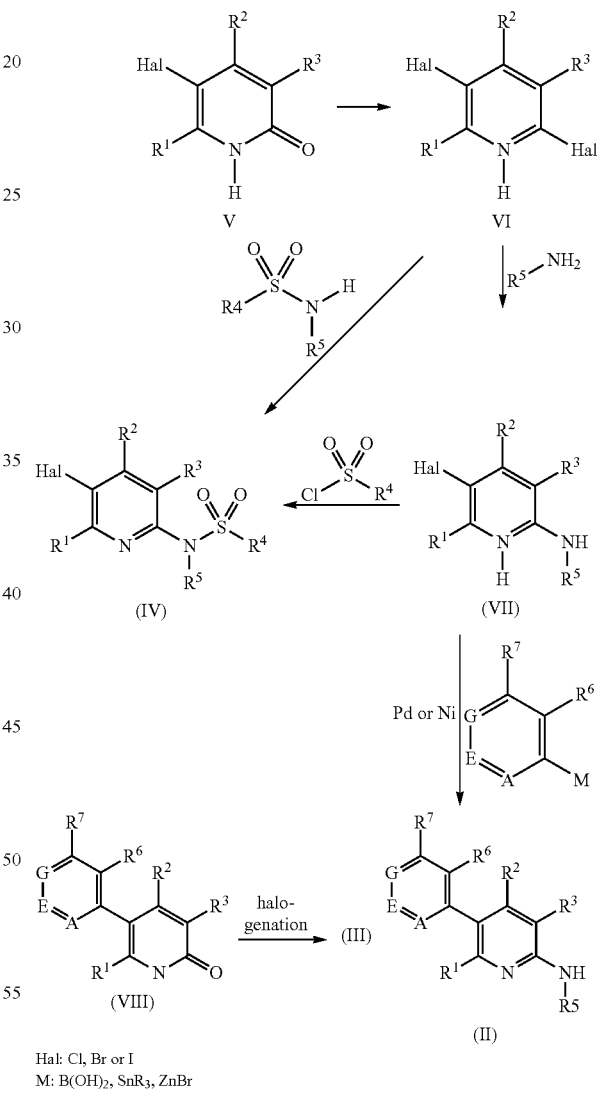

Hal: Cl, Br or I
M: B(OH)$_2$, SnR$_3$, ZnBr

Compounds of formula II can then be prepared from VII via a metal-catalysed (Pd or Ni) cross-coupling reaction with corresponding organometallic reagent such as (hetero)aryl-boron, (hetero)arylzink or (hetero)aryltin reagents using Suzuki-, Stille- or Negishi-type coupling reactions as described above. The amino group can optionally be protected with standard protecting groups such as BOC or pivaloyl prior to performing the cross-coupling reaction. Compounds of formula III are obtained from compounds of formula VIII (prepared from V via metal-catalysed cross-coupling as for II) by an halogenation reaction (as for the preparation of VI). Compounds of formula IV can be prepared from VI via a nucleophilic substitution reaction with a corresponding aryl, heteroaryl or heterocyclyl sulfonamide in a solvent such as DMSO or DMF in the presence of a base such as sodium hydride, at room temperature or at elevated temperature. The sulfonamides used in this step are either commercial, known in the literature or can be obtained by standard procedures known in the art. They can also first be converted into their sodium or potassium and these salts can then be used in the reaction, a procedure which does not require the addition of further base. Alternatively, IV can be obtained from VII by reacting with the corresponding aryl, heteroaryl or heterocyclyl sulfonyl chlorides as described above.

A preferred process for the preparation of a compound of formula I, wherein $R^1$ to $R^7$, A, E and G are defined as before comprises the reaction of a compound according to formula

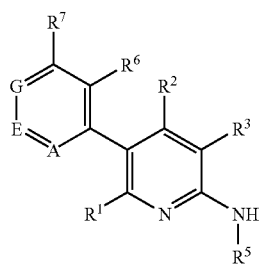

(II)

in the presence of a compound according to formula

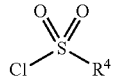

wherein $R^1$ to $R^7$, A, E and G are defined as before. Particularly preferred is the above process in the presence of a base such as trietylamine or (4-dimethylamino)-pyridine (DMAP) in a solvent such THF, ethanol, methylene chloride DMF or DMSO, or in pyridine as a solvent, with or without the addition of a base such as trietylamine or DMAP, at room temperature or at elevated temperatures.

Preferred intermediates are:
5-(2-chloro-phenyl)-pyridin-2-ylamine;
5-(2,4-dichloro-phenyl)-pyridin-2-ylamine;
5-(2-chloro-phenyl)-6-methyl-pyridin-2-ylamine;
5-(2-chloro-4-fluoro-phenyl)-pyridin-2-ylamine;
5-(3-fluoro-phenyl)-pyridin-2-ylamine;
5-(2,4-difluoro-phenyl)-pyridin-2-ylamine;
5-(4-methoxy-phenyl)-pyridin-2-ylamine;
5-(4-fluoro-phenyl)-pyridin-2-ylamine;
5-(2-methoxy-phenyl)-pyridin-2-ylamine;
5-(2-fluoro-phenyl)-pyridin-2-ylamine;
5-(2-chloro-phenyl)-pyridin-2-ylamine;
5-(4-methanesulfonyl-phenyl)-pyridin-2-ylamine;
5-(4-fluoro-phenyl)-6-methyl-pyridin-2-ylamine;
5-(3-fluoro-phenyl)-6-methyl-pyridin-2-ylamine;
5-(2,3-dichloro-phenyl)-pyridin-2-ylamine;
5-(4-fluoro-2-methyl-phenyl)-pyridin-2-ylamine;
5-(2,5-dichloro-phenyl)-pyridin-2-ylamine;
5-(2-fluoro-5-trifluoromethyl-phenyl)-pyridin-2-ylamine;
5-(2-trifluoromethyl-phenyl)-pyridin-2-ylamine;
5-(2,3-difluoro-phenyl)-pyridin-2-ylamine;
5-(2,4-bis-trifluoromethyl-phenyl)-pyridin-2-ylamine;
5-(4-fluoro-2-methyl-phenyl)-6-methyl-pyridin-2-ylamine;
5-(2,4-chloro-phenyl)-6-methyl-pyridin-2-ylamine;
5-(5-fluoro-2-methyl-phenyl)-pyridin-2-ylamine;
5-(5-chloro-2-methyl-phenyl)-pyridin-2-ylamine;
5-(6-Chloro-2-fluoro-3-methyl-phenyl)-pyridin-2-ylamine;
5-(5-Chloro-2-methyl-phenyl)-6-methyl-pyridin-2-ylamine;
5-(6-Chloro-2-fluoro-3-methyl-phenyl)-6-methyl-pyridin-2-ylamine;
5-(2,5-Dichloro-phenyl)-6-methyl-pyridin-2-ylamine;
5-(5-Fluoro-2-methyl-phenyl)-6-methyl-pyridin-2-ylamine;
5-(2-Chloro-4-fluoro-phenyl)-6-methyl-pyridin-2-ylamine;
5-(2,3-Dichloro-phenyl)-6-methyl-pyridin-2-ylamine;
5-(2-Fluoro-phenyl)-6-methyl-pyridin-2-ylamine;
5-(2-Chloro-phenyl)-3,4-dimethyl-pyridin-2-ylamine;
2-Methyl-[3,3']bipyridinyl-6-ylamine;
5-(2-Chloro-phenyl)-4-methyl-pyridin-2-ylamine and
5-(4-Fluoro-2-methyl-phenyl)-4-methyl-pyridin-2-ylamine A further preferred embodiment of the present invention is the use of a compound of the formula I as described above for the preparation of medicaments for the treatment and prophylaxis of diabetes, obesity, eating disorders, dyslipidemiae and hypertension.

Particularly preferred is the use of a compound according to formula I as described above for the preparation of medicaments for the treatment and prophylaxis of diabetes Type II.

Compounds as described above have $IC_{50}$ values below 1000 nM; preferred compounds have $IC_{50}$ values below 100 nM. More preferred compounds have $IC_{50}$ values below 10 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case.

In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

A solution of 0.2 g (0.98 mmol) of 5-(2-chloro-phenyl)-pyridin-2-ylamine and 0.23 g of 5-fluoro-2-methyl-benzenesulfonyl chloride (1.1 mmol) in pyridine (10 ml) was stirred at RT until completion of reaction according to HPLC analysis (48 h). After concentration in vacuo the residue was taken up in EtOAc, the solution washed with 1 N aqueous HCl, saturated brine then dried over sodium sulphate and concentrated in vacuo. The precipitate was collected by filtration and dried in a high vacuum to give 0.21 g (57%) of N-[5-(2-chloro-phenyl)-pyridin-2-yl]-5-fluoro-2-methyl-benzenesulfonamide as an off-white crystalline solid. ISN mass spectrum, m/e: 375.2 (M−1 calculated for $C_{18}H_{14}ClFN_2O_2S$: 375).

Preparation of the Starting Material:

A suspension of 70 mg (0.06 mmol) of tetrakis(triphenylphosphine) palladium(0) in benzene (4 ml) was treated at RT under an argon atmosphere successively with 0.35 g (2 mmol) of 2-amino-5-bromo-pyridine, 2.2 ml (4.4 mmol) of 2 M aqueous $Na_2CO_3$ solution, 0.34 g (2.2 mmol) of 2-chlorophenylboronic acid in ethanol (1 ml) and heated to reflux for 24 h. The reaction mixture was cooled and partitioned between EtOAc and water. The layers were separated, the organic layer dried over sodium sulphate and concentrated in vacuo. The residue was applied to a silica gel column with EtOAc as eluent. Combination of the purified fractions and concentration in vacuo gave 0.4 g (98%) of the desired 5-(2-chloro-phenyl)-pyridin-2-ylamine as white crystalline solid. ISP mass spectrum, m/e: 205.1 (M+1 calculated for $C_{11}H_9ClN_2$: 205).

Example 2

In analogy to example 1, on reaction of 5-(2-chloro-phenyl)-pyridin-2-ylamine with 3-chloro-2-methyl-benzenesulfonyl chloride there was obtained: 3-chloro-N-[5-(2-chloro-phenyl)-pyridin-2-yl]-2-methyl-benzenesulfonamide as an off-white solid. ISN mass spectrum, m/e: 391 (M−1 calculated for $C_{18}H_{14}Cl_2N_2O_2S$: 391).

Example 3

In analogy to example 1, on reaction of 5-(2,4-dichloro-phenyl)-pyridin-2-ylamine with 5-fluoro-2-methyl-benzenesulfonyl chloride there was obtained: N-[5-(2,4-dichloro-phenyl)-pyridin-2-yl]-5-fluoro-2-methyl-benzenesulfonamide as an off-white solid. ISN mass spectrum, m/e: 409 (M−1 calculated for $C_{18}H_{13}Cl_2FN_2O_2S$: 409).

Preparation of the Starting Material:

In analogy to example 1b), on reaction of 2-amino-5-bromo-pyridine with 2,4-dichlorophenylboronic acid there was obtained: 5-(2,4-dichloro-phenyl)-pyridin-2-ylamine as a white crystalline solid which was used without further purification in the subsequent reaction step.

Example 4a

In analogy to example 1, on reaction of 5-(2,4-dichloro-phenyl)-pyridin-2-ylamine with 3-chloro-2-methyl-benzenesulfonyl chloride there was obtained: 3-Chloro-N-[5-(2,4-dichloro-phenyl)-pyridin-2-yl]-2-methyl-benzenesulfonamide as an off-white solid. ISN mass spectrum, m/e: 425 (M−1 calculated for $C_{18}H_{13}Cl_3N_2O_2S$: 425).

Example 4b

In analogy to example 1, on reaction of 5-(2-chloro-phenyl)-6-methyl-pyridin-2-ylamine with 3-chloro-2-methyl-benzenesulfonyl chloride there was obtained: 3-Chloro-N-[5-(2-chloro-phenyl)-6-methyl-pyridin-2-yl]-2-methyl-benzenesulfonamide as a white solid. ISN mass spectrum, m/e: 405.1 (M−1 calculated for $C_{19}H_{16}Cl_2N_2O_2S$: 405).

Preparation of the Starting Material:

In analogy to example 1b), on reaction of 5-bromo-6-methyl-pyridin-2-ylamine with 2-chlorophenylboronic acid there was obtained: 5-(2-chloro-phenyl)-6-methyl-pyridin-2-ylamine as a white crystalline solid. ISP mass spectrum, m/e: 219.2 (M+1 calculated for $C_{12}H_{11}ClN_2$: 219).

Example 5

In analogy to example 1, on reaction of 5-(2-chloro-phenyl)-6-methyl-pyridin-2-ylamine with biphenyl-4-sulfonyl chloride there was obtained: Biphenyl-4-sulfonic acid [5-(2-chloro-phenyl)-6-methyl-pyridin-2-yl]-amide as a white foam. ISN mass spectrum, m/e: 433.2 (M−1 calculated for $C_{24}H_{19}ClN_2O_2S$: 433).

Example 6

In analogy to example 1, on reaction of 5-(2-chloro-4-fluoro-phenyl)-pyridin-2-ylamine with 3-chloro-2-methyl-benzenesulfonyl chloride there was obtained: 3-Chloro-N-[5-(2-chloro-4-fluoro-phenyl)-pyridin-2-yl]-2-methyl-benzenesulfonamide as an amorphous white solid. ISN mass spectrum, m/e: 409 (M−1 calculated for $C_{18}H_{13}Cl_2FN_2O_2S$: 409).

Preparation of the Starting Material:

In analogy to example 1b), on reaction of 5-bromo-pyridin-2-ylamine with 2-chloro-4-fluoro-phenylboronic acid there was obtained: 5-(2-chloro-4-fluoro-phenyl)-pyridin-2-ylamine as a white crystalline solid which was used without further purification in the next reaction step.

Example 7

In analogy to example 1, on reaction of 5-(3-fluoro-phenyl)-pyridin-2-ylamine with 3-chloro-2-methyl-benzenesulfonyl chloride there was obtained: 3-Chloro-N-[5-(3-fluoro-phenyl)-pyridin-2-yl]-2-methyl-benzenesulfonamide as a crystalline white solid. ISN mass spectrum, m/e: 375.2 (M−1 calculated for $C_{18}H_{14}ClFN_2O_2S$: 375).

Preparation of the Starting Material:

In analogy to example 1b), on reaction of 5-bromo-pyridin-2-ylamine with 3-fluoro-phenylboronic acid there was obtained: 5-(3-fluoro-phenyl)-pyridin-2-ylamine as a white crystalline solid which was used without further purification in the next reaction step.

Example 8

In analogy to example 1, on reaction of 5-(2,4-difluoro-phenyl)-pyridin-2-ylamine with 3-chloro-2-methyl-benzenesulfonyl chloride there was obtained: 3-Chloro-N-[5-(2,4-difluoro-phenyl)-pyridin-2-yl]-2-methyl-benzenesulfonamide as a crystalline white solid. ISN mass spectrum, m/e: 392.9 (M−1 calculated for $C_{18}H_{13}ClF_2N_2O_2S$: 392).

Preparation of the Starting Material:

In analogy to example 1b), on reaction of 5-bromo-pyridin-2-ylamine with 2,4-difluoro-phenylboronic acid there was obtained: 5-(2,4-difluoro-phenyl)-pyridin-2-ylamine as a white crystalline which was used without further purification in the next reaction step.

Example 9

In analogy to example 1, on reaction of 5-(2,4-difluoro-phenyl)-pyridin-2-ylamine with 5-fluoro-2-methyl-benzenesulfonyl chloride there was obtained: N-[5-(2,4-Difluoro-phenyl)-pyridin-2-yl]-5-fluoro-2-methyl-benzenesulfonamide as a crystalline white solid. ISN mass spectrum, m/e: 377.1 (M−1 calculated for $C_{18}H_{13}F_3N_2O_2S$: 377).

Example 10

In analogy to example 1, on reaction of 5-(4-methoxy-phenyl)-pyridin-2-ylamine with 3-chloro-2-methyl-benzenesulfonyl chloride there was obtained: 3-Chloro-N-[5-(4-methoxy-phenyl)-pyridin-2-yl]-2-methyl-benzenesulfonamide as a crystalline white solid. ISN mass spectrum, m/e: 387.1 (M−1 calculated for $C_{19}H_{17}ClN_2O_2S$: 387).

Preparation of the Starting Material:

In analogy to example 1b), on reaction of 5-bromo-pyridin-2-ylamine with 4-methoxy-phenylboronic acid there was obtained: 5-(4-methoxy-phenyl)-pyridin-2-ylamine as a beige crystalline solid which was used without further purification in the next reaction step.

Example 11

In analogy to example 1, on reaction of 5-(4-fluoro-phenyl)-pyridin-2-ylamine with 3-chloro-2-methyl-benzenesulfonyl chloride there was obtained: 3-Chloro-N-[5-(4-fluoro-phenyl)-pyridin-2-yl]-2-methyl-benzenesulfonamide as a crystalline white solid. ISN mass spectrum, m/e: 375.2 (M−1 calculated for $C_{18}H_{14}ClFN_2O_2S$: 375).

Preparation of the Starting Material:

In analogy to example 1b), on reaction of 5-bromo-pyridin-2-ylamine with 4-fluoro-phenylboronic acid there was obtained: 5-(4-fluoro-phenyl)-pyridin-2-ylamine as a brown crystalline solid which was used without further purification in the next reaction step.

Example 12

In analogy to example 1, on reaction of 5-(4-fluoro-phenyl)-pyridin-2-ylamine with 5-fluoro-2-methyl-benzenesulfonyl chloride there was obtained: 3-Chloro-N-[5-(4-fluoro-phenyl)-pyridin-2-yl]-2-methyl-benzenesulfonamide as a crystalline off-white solid. ISN mass spectrum, m/e: 359 (M−1 calculated for $C_{18}H_{14}F_2N_2O_2S$: 359).

Example 13

In analogy to example 1, on reaction of 5-(2-methoxy-phenyl)-pyridin-2-ylamine with 5-fluoro-2-methyl-benzenesulfonyl chloride there was obtained: 5-Fluoro-N-[5-(2-methoxy-phenyl)-pyridin-2-yl]-2-methyl-benzenesulfonamide as a crystalline white solid. ISN mass spectrum, m/e: 371.1 (M−1 calculated for $C_{19}H_{17}FN_2O_3S$: 371).

Preparation of the Starting Material:

In analogy to example 1b), on reaction of 5-bromo-pyridin-2-ylamine with 2-methoxy-phenylboronic acid there was obtained: 5-(2-methoxy-phenyl)-pyridin-2-ylamine as yellow oil which was used without further purification in the next reaction step.

Example 14

In analogy to example 1, on reaction of 5-(2-fluoro-phenyl)-pyridin-2-ylamine with 3-chloro-2-methyl-benzenesulfonyl chloride there was obtained: 3-Chloro-N-[5-(2-fluoro-phenyl)-pyridin-2-yl]-2-methyl-benzenesulfonamide as a crystalline white solid. ISN mass spectrum, m/e: 375.2 (M−1 calculated for $C_{18}H_{14}ClFN_2O_2S$: 375).

Preparation of the Starting Material:

In analogy to example 1b), on reaction of 5-bromo-pyridin-2-ylamine with 2-fluoro-phenylboronic acid there was obtained: 5-(2-fluoro-phenyl)-pyridin-2-ylamine as yellow oil which was used without further purification in the next reaction step.

Example 15

In analogy to example 1, on reaction of 5-(2-fluoro-phenyl)-pyridin-2-ylamine with 5-fluoro-2-methyl-benzenesulfonyl chloride there was obtained: 5-Fluoro-N-[5-(2-fluoro-phenyl)-pyridin-2-yl]-2-methyl-benzenesulfonamide as amorphous white solid. ISN mass spectrum, m/e: 359 (M−1 calculated for $C_{18}H_{14}F_2N_2O_2S$: 359).

Example 16

In analogy to example 1, on reaction of 5-(2-chloro-phenyl)-pyridin-2-ylamine with 2,4-dichloro-6-methyl-benzenesulfonyl chloride there was obtained: 2,4-Dichloro-N-[5-(2-chloro-phenyl)-pyridin-2-yl]-6-methyl-benzenesulfonamide as a colourless crystalline solid. ISP mass spectrum, m/e: 425 (M−1 calculated for $C_{18}H_{13}Cl_3N_2O_2S$: 425).

Example 17

In analogy to example 1, on reaction of 5-(2-chloro-phenyl)-pyridin-2-ylamine with 2,5-difluoro-benzenesulfonyl chloride there was obtained: N-[5-(2-chloro-phenyl)-pyridin-2-yl]-2,5-difluoro-benzenesulfonamide as a white crystalline solid. ISN mass spectrum, m/e: 379 (M−1 calculated for $C_{17}H_{11}ClF_2N_2O_2S$: 379).

Example 18

In analogy to example 1, on reaction of 5-(4-methanesulfonyl-phenyl)-pyridin-2-ylamine with 3-chloro-2-methyl-benzenesulfonyl chloride there was obtained: 3-Chloro-N-[5-(4-methanesulfonyl-phenyl)-pyridin-2-yl]-2-methyl-benzenesulfonamide as an amorphous white solid. ISN mass spectrum, m/e: 435.1 (M−1 calculated for $C_{19}H_{17}ClN_2O_4S_2$: 435).
Preparation of the Starting Material:
In analogy to example 1b), on reaction of 5-bromo-pyridin-2-ylamine with 4-methanesulfonyl-phenylboronic acid there was obtained: 5-(4-methanesulfonyl-phenyl)-pyridin-2-ylamine as a white crystalline solid which was used without further purification in the next reaction step.

Example 19

In analogy to example 1, on reaction of 5-(4-fluoro-phenyl)-6-methyl-pyridin-2-ylamine with 3-chloro-2-methyl-benzenesulfonyl chloride there was obtained: 3-Chloro-N-[5-(4-fluoro-phenyl)-6-methyl-pyridin-2-yl]-2-methyl-benzenesulfonamide as a yellow foam. ISN mass spectrum, m/e: 389 (M−1 calculated for $C_{19}H_{16}ClFN_2O_2S$: 389).
Preparation of the Starting Material:
In analogy to example 1b), on reaction of 5-bromo-6-methyl-pyridin-2-ylamine with 4-fluoro-phenylboronic acid there was obtained: 5-(4-fluoro-phenyl)-6-methyl-pyridin-2-ylamine as a yellow crystalline solid which was used without further purification in the next reaction step.

Example 20

In analogy to example 1, on reaction of 5-(4-fluoro-phenyl)-6-methyl-pyridin-2-ylamine with 5-fluoro-2-methyl-benzenesulfonyl chloride there was obtained: 5-Fluoro-N-[5-(4-fluoro-phenyl)-6-methyl-pyridin-2-yl]-2-methyl-benzenesulfonamide as a light-yellow foam. ISN mass spectrum, m/e: 373.1 (M−1 calculated for $C_{19}H_{16}F_2N_2O_2S$: 373).

Example 21

In analogy to example 1, on reaction of 5-(3-fluoro-phenyl)-6-methyl-pyridin-2-ylamine with 3-chloro-2-methyl-benzenesulfonyl chloride there was obtained: 3-Chloro-N-[5-(3-fluoro-phenyl)-6-methyl-pyridin-2-yl]-2-methyl-benzenesulfonamide as a yellow foam. ISN mass spectrum, m/e: 389.1 (M−1 calculated for $C_{19}H_{16}ClFN_2O_2S$: 389).
Preparation of the Starting Material:
In analogy to example 1b), on reaction of 5-bromo-6-methyl-pyridin-2-ylamine with 3-fluoro-phenylboronic acid there was obtained: 5-(3-fluoro-phenyl)-6-methyl-pyridin-2-ylamine as a white crystalline solid which was used without further purification in the next reaction step.

Example 22

In analogy to example 1, on reaction of 5-(3-fluoro-phenyl)-6-methyl-pyridin-2-ylamine with 5-fluoro-2-methyl-benzenesulfonyl chloride there was obtained: 5-Fluoro-N-[5-(3-fluoro-phenyl)-6-methyl-pyridin-2-yl]-2-methyl-benzenesulfonamide as a light-yellow foam. ISN mass spectrum, m/e: 373.1 (M−1 calculated for $C_{19}H_{16}F_2N_2O_2S$: 373).

Example 23

In analogy to example 1, on reaction of 5-(2,4-dichloro-phenyl)-pyridin-2-ylamine with 3,4-dimethoxy-benzenesulfonyl chloride there was obtained: N-[5-(2,4-Dichloro-phenyl)-pyridin-2-yl]-3,4-dimethoxy-benzenesulfonamide as a light-yellow foam. ISN mass spectrum, m/e: 437.1 (M−1 calculated for $C_{19}H_{16}Cl_2N_2O_4S$: 437).

Example 24

In analogy to example 1, on reaction of 5-(2,4-dichloro-phenyl)-pyridin-2-ylamine with 3,4-dichloro-benzenesulfonyl chloride there was obtained: 3,4-Dichloro-N-[5-(2,4-dichloro-phenyl)-pyridin-2-yl]-benzenesulfonamide as an crystalline white solid. ISN mass spectrum, m/e: 446.9 (M−1 calculated for $C_{17}H_{10}Cl_4N_2O_2S$: 447).

Example 25

In analogy to example 1, on reaction of 5-(2,3-dichloro-phenyl)-pyridin-2-ylamine with 2,5-difluoro-benzenesulfonyl chloride there was obtained: N-[5-(2,3-dichloro-phenyl)-pyridin-2-yl]-2,5-difluoro-benzenesulfonamide as a light-red solid. ISN mass spectrum, m/e: 413 (M−1 calculated for $C_{17}H_{10}Cl_2F_2N_2O_2S$: 413).
Preparation of the Starting Material:
In analogy to example 1b), on reaction of 5-bromo-pyridin-2-ylamine with 2,3-dichloro-phenylboronic acid there was obtained: 5-(2,3-dichloro-phenyl)-pyridin-2-ylamine as an off-white crystalline solid. EI mass spectrum, m/e: 239.1 (M calculated for $C_{11}H_8Cl_2N_2$: 239).

Example 26

In analogy to example 1, on reaction of 5-(2,3-dichloro-phenyl)-pyridin-2-ylamine with 3-chloro-2-methyl-benzenesulfonyl chloride there was obtained: 3-Chloro-N-[5-(2,3-dichloro-phenyl)-pyridin-2-yl]-2-methyl-benzenesulfonamide as a white solid. ISN mass spectrum, m/e: 427 (M−1 calculated for $C_{18}H_{13}Cl_3N_2O_2S$: 427).

Example 27

In analogy to example 1, on reaction of 5-(2-chloro-phenyl)-pyridin-2-ylamine with 3,4-dichloro-benzenesulfonyl chloride there was obtained: 3,4-dichloro-N-[5-(2-chloro-phenyl)-pyridin-2-yl]-benzenesulfonamide as a white crystalline solid. ISN mass spectrum, m/e: 411 (M−1 calculated for $C_{17}H_{11}Cl_3N_2O_2S$: 411).

Example 28

In analogy to example 1, on reaction of 5-(2-chloro-phenyl)-pyridin-2-ylamine with 3,4-dimethoxy-benzenesulfonyl chloride there was obtained: N-[5-(2-Chloro-phenyl)-pyridin-2-yl]-3,4-dimethoxy-benzenesulfonamide as a white crystalline solid. ISN mass spectrum, m/e: 403.2 (M−1 calculated for $C_{19}H_{17}ClN_2O_4S$: 403).

Example 29

In analogy to example 1, on reaction of 5-(2-chloro-phenyl)-pyridin-2-ylamine with 3-chloro-4-methyl-benzenesulfonyl chloride there was obtained: 3-Chloro-N-[5-(2-chloro-phenyl)-pyridin-2-yl]-4-methyl-benzenesulfonamide as a white crystalline solid. ISN mass spectrum, m/e: 391 (M+1 calculated for $C_{18}H_{14}Cl_2N_2O_4S$: 391).

Example 30

In analogy to example 1, on reaction of 5-(4-fluoro-2-methyl-phenyl)-pyridin-2-ylamine with 5-fluoro-2-methylbenzenesulfonyl chloride there was obtained: 5-Fluoro-N-[5-(4-fluoro-2-methyl-phenyl)-pyridin-2-yl]-2-methyl-benzenesulfonamide as a light-yellow solid. ISN mass spectrum, m/e: 373 (M−1 calculated for $C_{19}H_{16}F_2N_2O_2S$: 373).

Preparation of the Starting Material:

In analogy to example 1b), on reaction of 5-bromo-pyridin-2-ylamine with 4-fluoro-2-methyl-phenylboronic acid there was obtained: 5-(4-fluoro-2-methyl-phenyl)-pyridin-2-ylamine as a white solid. ISP mass spectrum, m/e: 203.1 (M+1 calculated for $C_{12}H_{11}FN_2$: 203).

Example 31

In analogy to example 1, on reaction of 5-(4-fluoro-2-methyl-phenyl)-pyridin-2-ylamine with 3-chloro-2-methyl-benzenesulfonyl chloride there was obtained: 3-Chloro-N-[5-(4-fluoro-2-methyl-phenyl)-pyridin-2-yl]-2-methyl-benzenesulfonamide as a light-yellow solid. ISN mass spectrum, m/e: 389.1 (M−1 calculated for $C_{19}H_{16}ClFN_2O_2S$: 389).

Example 32

In analogy to example 1, on reaction of 5-(2-chloro-phenyl)-pyridin-2-ylamine with 3-chloro-4-methoxy-benzenesulfonyl chloride there was obtained: 3-Chloro-N-[5-(2-chloro-phenyl)-pyridin-2-yl]-4-methoxy-benzenesulfonamide as a white solid. ISP mass spectrum, m/e: 409.2 (M+1 calculated for $C_{18}H_{14}Cl_2N_2O_3S$: 409).

Example 33

In analogy to example 1, on reaction of 5-(2-chloro-phenyl)-pyridin-2-ylamine with 4,5-dichloro-2-fluoro-benzenesulfonyl chloride there was obtained: 4,5-Dichloro-N-[5-(2-chloro-phenyl)-pyridin-2-yl]-2-fluoro-benzenesulfonamide as a white solid. ISP mass spectrum, m/e: 431.2 (M+1 calculated for $C_{17}H_{10}Cl_3FN_2O_3S$: 431).

Example 34

In analogy to example 1, on reaction of 5-(2,4-dichloro-phenyl)-pyridin-2-ylamine with 3-chloro-4-methoxy-benzenesulfonyl chloride there was obtained: 3-Chloro-N-[5-(2,4-dichloro-phenyl)-pyridin-2-yl]-4-methoxy-benzenesulfonamide as an crystalline white solid. ISP mass spectrum, m/e: 443.1 (M+1 calculated for $C_{18}H_{13}Cl_3N_2O_3S$: 443).

Example 35

In analogy to example 1, on reaction of 5-(2,4-dichloro-phenyl)-pyridin-2-ylamine with 3-chloro-4-methyl-benzenesulfonyl chloride there was obtained: 3-Chloro-N-[5-(2,4-dichloro-phenyl)-pyridin-2-yl]-4-methyl-benzenesulfonamide as an crystalline white solid. ISP mass spectrum, m/e: 427.2 (M+1 calculated for $C_{18}H_{13}Cl_3N_2O_2S$: 427).

Example 36

A solution of 0.23 g (1 mmol) of 5-(2,4-dichloro-phenyl)-pyridin-2-ylamine and 0.2 g (1.1 mmol) of piperidine-1-sulfonyl chloride (preparation: Bull. Soc. Chim. Fr.; 1936, p 2143) in pyridine (10 ml) was heated to reflux until completion of reaction according to HPLC analysis (20 h). After concentration in vacuo the residue was taken up in EtOAc, which was then washed with 1N aqueous HCl, saturated brine, dried over sodium sulphate and concentrated in vacuo. The residue was applied to a silica gel column with EtOAc/toluene (9/1 to 1/1) as eluent. Combination of the purified fractions and concentration in vacuo gave 0.26 g (67%) of the desired piperidine-1-sulfonic acid [5-(2,4-dichloro-phenyl)-pyridin-2-yl]-amide as a brown crystalline solid. ISN mass spectrum, m/e: 384 (M−1 calculated for $C_{16}H_{17}Cl_2N_2O_2S$: 384).

Example 37

In analogy to example 1, on reaction of 5-(2,3-dichloro-phenyl)-pyridin-2-ylamine with 2-trifluoromethyl-benzenesulfonyl chloride there was obtained: N-[5-(2,3-Dichloro-phenyl)-pyridin-2-yl]-2-trifluoromethyl-benzenesulfonamide as a light-red solid. ISN mass spectrum, m/e: 445 (M−1 calculated for $C_{18}H_{11}Cl_2F_3N_2O_2S$: 445).

Example 38

In analogy to example 1, on reaction of 5-(2,3-dichloro-phenyl)-pyridin-2-ylamine with 4-fluoro-benzenesulfonyl chloride there was obtained: N-[5-(2,3-Dichloro-phenyl)-pyridin-2-yl]-4-fluoro-benzenesulfonamide as a white solid. ISN mass spectrum, m/e: 395 (M−1 calculated for $C_{17}H_{11}Cl_2FN_2O_2S$: 395).

Example 39

In analogy to example 1, on reaction of 5-(2,5-dichloro-phenyl)-pyridin-2-ylamine with 2,5-difluoro-benzenesulfonyl chloride there was obtained: N-[5-(2,5-Dichloro-phenyl)-pyridin-2-yl]-2,5-difluoro-benzenesulfonamide as a light yellow amorphous solid. ISN mass spectrum, m/e: 413 (M−1 calculated for $C_{17}H_{10}Cl_2F_2N_2O_2S$: 413).

Preparation of the Starting Material:

In analogy to example 1b), on reaction of 5-bromo-pyridin-2-ylamine with 2,3-dichloro-phenylboronic acid there was obtained: 5-(2,5-dichloro-phenyl)-pyridin-2-ylamine as an off-white crystalline solid. EI mass spectrum, m/e: 239.1 (M calculated for $C_{11}H_8Cl_2N_2$: 239).

Example 40

In analogy to example 1, on reaction of 5-(2,5-dichloro-phenyl)-pyridin-2-ylamine with 5-fluoro-2-methyl-benzenesulfonyl chloride there was obtained: N-[5-(2,5-Dichloro-phenyl)-pyridin-2-yl]-5-fluoro-2-methyl-benzenesulfonamide as an off-white solid. ISN mass spectrum, m/e: 409 (M−1 calculated for $C_{18}H_{13}Cl_2FN_2O_2S$: 409).

Example 41

In analogy to example 1, on reaction of 5-(2,5-dichloro-phenyl)-pyridin-2-ylamine with 3-chloro-2-methyl-benzenesulfonyl chloride there was obtained: 3-Chloro-N-[5-(2,5-dichloro-phenyl)-pyridin-2-yl]-2-methyl-benzenesulfonamide as a white solid. ISN mass spectrum, m/e: 427.1 (M−1 calculated for $C_{18}H_{13}Cl_3N_2O_2S$: 427).

Example 42

In analogy to example 1, on reaction of 5-(2-fluoro-5-trifluoromethyl-phenyl)-pyridin-2-ylamine with 5-fluoro-2- methyl-benzenesulfonyl chloride there was obtained: 5-Fluoro-N-[5-(2-fluoro-5-trifluoromethyl-phenyl)-pyridin-2-yl]-2-methyl-benzenesulfonamide as a white solid. ISN mass spectrum, m/e: 427.2 (M−1 calculated for $C_{19}H_{13}F_5N_2O_2S$: 427).

Preparation of the Starting Material:

In analogy to example 1b), on reaction of 5-bromo-pyridin-2-ylamine with 2-fluoro-5-trifluoromethyl-phenylboronic acid there was obtained: 5-(2-fluoro-5-trifluoromethyl-phenyl)-pyridin-2-ylamine as a white solid. ISP mass spectrum, m/e: 257 (M+H calculated for $C_{12}H_8F_4N_2$: 257).

Example 43

In analogy to example 1, on reaction of 5-(2-fluoro-5-trifluoromethyl-phenyl)-pyridin-2-ylamine with 3-chloro-2-methyl-benzenesulfonyl chloride there was obtained: 3-Chloro-N-[5-(2-fluoro-5-trifluoromethyl-phenyl)-pyridin-2-yl]-2-methyl-benzenesulfonamide as a white solid ISN mass spectrum, m/e: 442.9 (M−1 calculated for $C_{19}H_{13}ClF_4N_2O_2S$: 443).

Example 44

In analogy to example 1, on reaction of 5-(2-trifluoromethyl-phenyl)-pyridin-2-ylamine with 3-chloro-2-methyl-benzenesulfonyl chloride there was obtained: 3-Chloro-2-methyl-N-[5-(2-trifluoromethyl-phenyl)-pyridin-2-yl]-benzenesulfonamide as an orange solid. ISN mass spectrum, m/e: 425 (M−1 calculated for $C_{19}H_{14}ClF_3N_2O_2S$: 425).

Preparation of the Starting Material:

In analogy to example 1b), on reaction of 5-bromo-pyridin-2-ylamine with 2-trifluoromethyl-phenylboronic acid there was obtained: 5-(2-trifluoromethyl-phenyl)-pyridin-2-ylamine as a white solid. ISP mass spectrum, m/e: 239.2 (M+H calculated for $C_{12}H_9F_3N_2$: 239).

Example 45

In analogy to example 1, on reaction of 5-(2-trifluoromethyl-phenyl)-pyridin-2-ylamine with 3-chloro-4-methyl-benzenesulfonyl chloride there was obtained: 3-Chloro-4-methyl-N-[5-(2-trifluoromethyl-phenyl)-pyridin-2-yl]-benzenesulfonamide as a light-grey solid. ISP mass spectrum, m/e: 425 (M−1 calculated for $C_{19}H_{14}ClF_3N_2O_2S$: 425).

Example 46

In analogy to example 1, on reaction of 5-(2,4-dichloro-phenyl)-pyridin-2-ylamine with 5-chloro-2-methoxy-benzenesulfonyl chloride there was obtained: 5-chloro-N-[5-(2,4-dichloro-phenyl)-pyridin-2-yl]-2-methoxy-benzenesulfonamide as a crystalline white solid. ISP mass spectrum, m/e: 443.1 (M+1 calculated for $C_{18}H_{13}Cl_3N_2O_3S$: 443).

Example 47

In analogy to example 1, on reaction of 5-(2,4-dichloro-phenyl)-pyridin-2-ylamine with 4-acetylamino-3-chloro-benzenesulfonyl chloride there was obtained: N-{2-Chloro-4-[5-(2,4-dichloro-phenyl)-pyridin-2-ylsulfamoyl]-phenyl}-acetamide as a crystalline brown solid. ISN mass spectrum, m/e: 468 (M−1 calculated for $C_{19}H_{14}Cl_3N_3O_3S$: 468).

Example 48

In analogy to example 1, on reaction of 5-(2,4-dichloro-phenyl)-pyridin-2-ylamine with 4-trifluoromethyl-benzene-sulfonyl chloride there was obtained: N-[5-(2,4-Dichloro-phenyl)-pyridin-2-yl]-4-trifluoromethyl-benzenesulfonamide as a crystalline white solid. ISN mass spectrum, m/e: 445 (M−1 calculated for $C_{18}H_{11}Cl_2F_3N_2O_2S$: 445)

Example 49

In analogy to example 1, on reaction of 5-(2,4-dichloro-phenyl)-pyridin-2-ylamine with 4-methylsulfonyl-benzenesulfonyl chloride there was obtained: N-[5-(2,4-Dichloro-phenyl)-pyridin-2-yl]-4-methysulfonyl-benzenesulfonamide as a crystalline light-brown solid. ISN mass spectrum, m/e: 455.1 (M−1 calculated for $C_{18}H_{14}Cl_2N_2O_4S_2$: 455).

Example 50

In analogy to example 1, on reaction of 5-(2,3-difluoro-phenyl)-pyridin-2-ylamine with 3-chloro-4-methyl-benzenesulfonyl chloride there was obtained: 3-Chloro-N-[5-(2,3-difluoro-phenyl)-pyridin-2-yl]-4-methyl-benzenesulfonamide as a white solid. ISN mass spectrum, m/e: 392.9 (M−1 calculated for $C_{18}H_{13}ClF_2N_2O_2S$: 393).

Preparation of the Starting Material:

In analogy to example 1b), on reaction of 5-bromo-pyridin-2-ylamine with 2,3-difluoro-phenylboronic acid there was obtained: 5-(2,3-difluoromethyl-phenyl)-pyridin-2-ylamine as a white solid. ISP mass spectrum, m/e: 207.2 (M+H calculated for $C_{11}H_8F_2N_2$: 207).

Example 51

In analogy to example 1, on reaction of 5-(2,3-difluoro-phenyl)-pyridin-2-ylamine with 3-fluoro-2-methyl-benzene-sulfonyl chloride there was obtained: N-[5-(2,3-Difluoro-phenyl)-pyridin-2-yl]-5-fluoro-2-methyl-benzenesulfonamide as a white solid. ISN mass spectrum, m/e: x377.2 (M−1 calculated for $C_{18}H_{13}F_3N_2O_2S$: 377).

Example 52

In analogy to example 1, on reaction of 5-(2,4-bis-trifluoromethyl-phenyl)-pyridin-2-ylamine with 3-chloro-2-methyl-benzenesulfonyl chloride there was obtained: N-[5-(2,4-Bis-trifluoromethyl-phenyl)-pyridin-2-yl]-3-chloro-2-methyl-benzenesulfonamide as a white solid. ISN mass spectrum, m/e: 493 (M−1 calculated for $C_{20}H_{13}ClF_6N_2O_2S$: 493).

Preparation of the Starting Material:

In analogy to example 1b), on reaction of 5-bromo-pyridin-2-ylamine with 2,4-bis-trifluoromethyl-phenylboronic acid there was obtained: 5-(2,4-bis-trifluoromethyl-phenyl)-pyridin-2-ylamine as a white solid. ISP mass spectrum, m/e: 307.2 (M+1 calculated for $C_{13}H_8F_6N_2$: 307).

Example 53

In analogy to example 1, on reaction of 5-(2,4-bis-trifluoromethyl-phenyl)-pyridin-2-ylamine with 3-chloro-4-methyl-benzenesulfonyl chloride there was obtained: N-[5-(2,4-Bis-trifluoromethyl-phenyl)-pyridin-2-yl]-3-chloro-4-methyl-benzenesulfonamide as a white solid. ISN mass spectrum, m/e: 493 (M−1 calculated for $C_{20}H_{13}ClF_6N_2O_2S$: 493).

Example 54

In analogy to example 1, on reaction of 5-(2,3-difluoro-phenyl)-pyridin-2-ylamine with 3-chloro-2-methyl-benzenesulfonyl chloride there was obtained: 3-Chloro-N-[5-(2,3-difluoro-phenyl)-pyridin-2-yl]-2-methyl-benzenesulfonamide as a white solid. ISN mass spectrum, m/e: 392 (M−1 calculated for $C_{18}H_{13}ClF_2N_2O_2S$: 392).

Example 55

In analogy to example XX, on reaction of 5-(2,3-dichloro-phenyl)-pyridin-2-ylamine with piperidine-1-sulfonyl chloride there was obtained: Piperidine-1-sulfonic acid [5-(2,3-dichloro-phenyl)-pyridin-2-yl]-amide as an off-white solid. ISN mass spectrum, m/e: 384 (M−1 calculated for $C_{16}H_{17}Cl_2N_3O_2S$: 384).

Example 56

In analogy to example 1, on reaction of 5-(4-fluoro-phenyl)-6-methyl-pyridin-2-ylamine with 5-chloro-2-methoxy-benzenesulfonyl chloride there was obtained: 5-Chloro-N-[5-(4-fluoro-phenyl)-6-methyl-pyridin-2-yl]-2-methoxy-benzenesulfonamide as a crystalline white solid. ISN mass spectrum, m/e: 405.2 (M−1 calculated for $C_{19}H_{16}ClFN_2O_3S$: 405).

Example 57

In analogy to example 1, on reaction of 5-(4-fluoro-phenyl)-6-methyl-pyridin-2-ylamine with 4-acetylamino-3-chloro-benzenesulfonyl chloride there was obtained: N-{2-Chloro-4-[5-(4-fluoro-phenyl)-6-methyl-pyridin-2-ylsulfamoyl]-phenyl}-acetamide as a light-brown solid. ISN mass spectrum, m/e: 432.2 (M−1 calculated for $C_{20}H_{17}ClFN_3O_3S$: 432).

Example 58

In analogy to example 1, on reaction of 5-(4-fluoro-phenyl)-6-methyl-pyridin-2-ylamine with 4-trifluormethyl-benzenesulfonyl chloride there was obtained: N-[5-(4-Fluoro-phenyl)-6-methyl-pyridin-2-yl]-4-trifluoromethyl-benzenesulfonamide as a brown foam. ISN mass spectrum, m/e: 409 (M−1 calculated for $C_{19}H_{14}F_4N_2O_2S$: 409).

Example 59

In analogy to example 1, on reaction of 5-(4-fluoro-phenyl)-6-methyl-pyridin-2-ylamine with 4-methanesulfonyl-benzenesulfonyl chloride there was obtained: N-[5-(4-Fluoro-phenyl)-6-methyl-pyridin-2-yl]-4-methanesulfonyl-benzenesulfonamide as a brown viscous oil. ISN mass spectrum, m/e: 419 (M−1 calculated for $C_{19}H_{17}FN_2O_4S_2$: 419).

Example 60

In analogy to example 1, on reaction of 5-(2,3-dichloro-phenyl)-pyridin-2-ylamine with (4-chlorosulfonyl-phenoxy)-acetic acid methyl ester there was obtained: {4-[5-(2,3-dichloro-phenyl)-pyridin-2-ylsulfamoyl]-phenoxy}-acetic acid methyl ester as a white solid. ISN mass spectrum, m/e: 465 (M−1 calculated for $C_{20}H_{16}Cl_2N_2O_5S$: 465).

Example 61

In analogy to example 1, on reaction of 5-(4-fluoro-phenyl)-6-methyl-pyridin-2-ylamine with 4-trifluoromethoxy-benzenesulfonyl chloride there was obtained: N-[5-(4-Fluorophenyl)-6-methyl-pyridin-2-yl]-4-trifluoromethoxy-benzenesulfonamide as a light-brown foam. ISP mass spectrum, m/e: 427.3 (M+1 calculated for $C_{19}H_{14}F_4N_2O_3S$: 427).

Example 62

In analogy to example 1, on reaction of 5-(4-fluoro-phenyl)-6-methyl-pyridin-2-ylamine with 3-chloro-4-methoxy-benzenesulfonyl chloride there was obtained: 3-Chloro-N-[5-(4-fluoro-phenyl)-6-methyl-pyridin-2-yl]-4-methoxy-benzenesulfonamide as a light-brown foam. ISN mass spectrum, m/e: 405.1 (M−1 calculated for $C_{19}H_{16}ClFN_2O_3S$: 405).

Example 63

In analogy to example 1, on reaction of 5-(4-fluoro-phenyl)-6-methyl-pyridin-2-ylamine with 4-chloro-2,5-dimethyl-benzenesulfonyl chloride there was obtained: 4-Chloro-N-[5-(4-fluoro-phenyl)-6-methyl-pyridin-2-yl]-2,5-dimethyl-benzenesulfonamide as a light-brownfoam. ISN mass spectrum, m/e: 403.1 (M−1 calculated for $C_{20}H_{18}ClFN_2O_2S$: 403).

Example 64

A solution of 120 mg (2.6 mmol) of 4-[5-(2,3-Dichloro-phenyl)-pyridin-2-ylsulfamoyl]-phenoxy}-acetic acid methyl ester, product of example 60, in THF/EtOH (each 5 ml) was treated with 57 mg (5.1 mmol) of $CaCl_2$, cooled to 0° C. and then 39 mg (1 mmol) of sodium borohydride were added portionwise. The mixture was stirred for 12 h at RT, poured into ice/water acidified with 3 M HCl to pH 1 and extracted with AcOEt. The layers were separated, the organic layer dried over sodium sulphate and concentrated in vacuo. The residue was applied to a silica gel column with EtOAc/heptan (1/1) then $CH_2Cl_2$/MeOH (95/5) as eluent. Combination of the purified fractions and concentration in vacuo gave 0.1 g (93%) of the desired N-[5-(2,3-Dichloro-phenyl)-pyridin-2-yl]-4-(2-hydroxy-ethoxy)-benzenesulfonamide as white foam. ISN mass spectrum, m/e: 437.2 (M−1 calculated for $C_{19}H_{16}Cl_2N_2O_4S$: 437).

Example 65

In analogy to example 1, on reaction of 5-(2-chloro-phenyl)-6-methyl-pyridin-2-ylamine with 4-fluoro-benzenesulfonyl chloride there was obtained: N-[5-(2-Chloro-phenyl)-6-methyl-pyridin-2-yl]-4-fluoro-benzenesulfonamide as a white foam. ISN mass spectrum, m/e: 375.2 (M−1 calculated for $C_{18}H_{14}ClFN_2O_2S$: 375).

Example 66

In analogy to example 1, on reaction of 5-(2-chloro-phenyl)-6-methyl-pyridin-2-ylamine with 3-chloro-4-methyl-benzenesulfonyl chloride there was obtained: 3-Chloro-N-[5-(2-chloro-phenyl)-6-methyl-pyridin-2-yl]-4-methyl-benzenesulfonamide as a white foam. ISN mass spectrum, m/e: 405.2 (M−1 calculated for $C_{19}H_{16}Cl_2N_2O_2S$: 405).

Example 67

In analogy to example 1, on reaction of 5-(2-chloro-phenyl)-6-methyl-pyridin-2-ylamine with 4-chloro-benzenesulfonyl chloride there was obtained: 4-Chloro-N-[5-(2- chloro-phenyl)-6-methyl-pyridin-2-yl]-benzenesulfonamide as a white foam. ISN mass spectrum, m/e: 391 (M−1 calculated for $C_{18}H_{14}Cl_2N_2O_2S$: 391).

Example 68

In analogy to example 1, on reaction of 5-(2-chloro-phenyl)-6-methyl-pyridin-2-ylamine with 4,6-dichloro-2-methyl-benzenesulfonyl chloride there was obtained: 2,4-Dichloro-N-[5-(2-chloro-phenyl)-6-methyl-pyridin-2-yl]-6-methyl-benzenesulfonamide as a white foam. ISN mass spectrum, m/e: 439 (M−1 calculated for $C_{19}H_{15}Cl_3N_2O_2S$: 439).

Example 69

In analogy to example 36, on reaction of 5-(2-chloro-phenyl)-6-methyl-pyridin-2-ylamine with 4 piperidine-1-sulfonyl chloride there was obtained: Piperidine-1-sulfonic acid [5-(2-chloro-phenyl)-6-methyl-pyridin-2-yl]-amide as a white foam. ISN mass spectrum, m/e: 364 (M−1 calculated for $C_{17}H_{20}ClN_3O_2S$: 364).

Example 70

In analogy to example 1, on reaction of 5-(2,4-dichloro-phenyl)-pyridin-2-ylamine with 4-fluoro-benzenesulfonyl chloride there was obtained: N-[5-(2,4-Dichloro-phenyl)-pyridin-2-yl]-4-fluoro-benzenesulfonamide as a crystalline white solid. ISN mass spectrum, m/e: 394.9 (M−1 calculated for $C_{17}H_{11}Cl_2FN_2O_2S$: 395).

Example 71

In analogy to example 1, on reaction of 5-(2,4-dichloro-phenyl)-pyridin-2-ylamine with 4-chloro-2,5-dimethyl-benzenesulfonyl chloride there was obtained: 4-Chloro-N-[5-(2,4-dichloro-phenyl)-pyridin-2-yl]-2,5-dimethyl-benzenesulfonamide as an amorphous white solid. ISN mass spectrum, m/e: 439 (M−1 calculated for $C_{19}H_{15}Cl_3N_2O_2S$: 439).

Example 72

In analogy to example 1, on reaction of 5-(2,4-dichloro-phenyl)-pyridin-2-ylamine with 2,4-difluoro-benzenesulfonyl chloride there was obtained: N-[5-(2,4-dichloro-phenyl)-pyridin-2-yl]-2,4-difluoro-benzenesulfonamide as a crystalline white solid. ISN mass spectrum, m/e: 413.1 (M−1 calculated for $C_{17}H_{10}Cl_2F_2N_2O_2S$: 413).

Example 73

In analogy to example 1, on reaction of 5-(2,4-dichloro-phenyl)-pyridin-2-ylamine with 2,4-dichloro-5-methyl-benzenesulfonyl chloride there was obtained: 2,4-Dichloro-N-[5-(2,4-dichloro-phenyl)-pyridin-2-yl]-5-methyl-benzenesulfonamide as a amorphous white solid. ISN mass spectrum, m/e: 459 (M−1 calculated for $C_{18}H_{12}Cl_4F_2N_2O_2S$: 459).

Example 74

In analogy to example 1, on reaction of 5-(2,3-dichloro-phenyl)-pyridin-2-ylamine with 3-trifluoromethyl-benzenesulfonyl chloride there was obtained: N-[5-(2,3-Dichloro-phenyl)-pyridin-2-yl]-3-trifluoromethyl-benzenesulfonamide as an off-white solid. ISN mass spectrum, m/e: 445 (M−1 calculated for $C_{18}H_{11}Cl_2F_3N_2O_2S$: 445).

Example 75

In analogy to example 1, on reaction of 5-(4-fluoro-2-methyl-phenyl)-6-methyl-pyridin-2-ylamine with 4-fluoro-benzenesulfonyl chloride there was obtained: 4-Fluoro-N-[5-(4-fluoro-2-methyl-phenyl)-6-methyl-pyridin-2-yl]-benzenesulfonamide as a white foam. ISN mass spectrum, m/e: 373.1 (M−1 calculated for $C_{19}H_{16}F_2N_2O_2S$: 373).
Preparation of the Starting Material:
In analogy to example 1b), on reaction of 5-bromo-6-methyl-pyridin-2-ylamine with 4-fluoro-2-methyl-phenylboronic acid there was obtained: 5-(4-Fluoro-2-methyl-phenyl)-6-methyl-pyridin-2-ylamine as a yellow solid which was used directly in the next reaction step.

Example 76

In analogy to example 1, on reaction of 5-(4-fluoro-2-methyl-phenyl)-6-methyl-pyridin-2-ylamine with 3-chloro-2-methyl-benzenesulfonyl chloride there was obtained: 3-Chloro-N-[5-(4-fluoro-2-methyl-phenyl)-6-methyl-pyridin-2-yl]-2-methyl-benzenesulfonamide as a white foam. ISN mass spectrum, m/e: 403.2 (M−1 calculated for $C_{20}H_{18}ClFN_2O_2S$: 403).

Example 77

In analogy to example 1, on reaction of 5-(4-fluoro-2-methyl-phenyl)-6-methyl-pyridin-2-ylamine with 5-fluoro-2-methyl-benzenesulfonyl chloride there was obtained: 5-Fluoro-N-[5-(4-fluoro-2-methyl-phenyl)-6-methyl-pyridin-2-yl]-2-methyl-benzenesulfonamide as a white solid. ISN mass spectrum, m/e: 387.1 (M−1 calculated for $C_{20}H_{18}F_2N_2O_2S$: 387).

Example 78

In analogy to example 1, on reaction of 5-(2,3-dichloro-phenyl)-pyridin-2-ylamine with 3-chloro-4-methyl-benzenesulfonyl chloride there was obtained: 3-Chloro-N-[5-(2,3-dichloro-phenyl)-pyridin-2-yl]-4-methyl-benzenesulfonamide as a white solid. ISN mass spectrum, m/e: 425 (M−1 calculated for $C_{18}H_{13}Cl_3N_2O_2S$: 425).

Example 79

In analogy to example 1, on reaction of 5-(2,3-dichloro-phenyl)-pyridin-2-ylamine with 4-trifluoromethyl-benzenesulfonyl chloride there was obtained: N-[5-(2,3-Dichloro-phenyl)-pyridin-2-yl]-4-trifluoromethyl-benzenesulfonamide as a white solid. ISN mass spectrum, m/e: 444.9 (M−1 calculated for $C_{18}H_{11}Cl_2F_3N_2O_2S$: 445).

Example 80

In analogy to example 1, on reaction of 5-(4-fluoro-2-methyl-phenyl)-6-methyl-pyridin-2-ylamine with 3-chloro-4-methyl-benzenesulfonyl chloride there was obtained: 3-Chloro-N-[5-(4-fluoro-2-methyl-phenyl)-6-methyl-pyridin-2-yl]-4-methyl-benzenesulfonamide as a white solid. ISN mass spectrum, m/e: 389 (M−1 calculated for $C_{19}H_{16}ClFN_2O_2S$: 389).

Example 81

In analogy to example 1, on reaction of 5-(4-fluoro-2-methyl-phenyl)-pyridin-2-ylamine with 3-trifluoromethylbenzenesulfonyl chloride there was obtained: N-[5-(4-Fluoro-2-methyl-phenyl)-pyridin-2-yl]-3-trifluoromethyl-benzenesulfonamide as a white solid. ISN mass spectrum, m/e: 409 (M−1 calculated for $C_{19}H_{14}F_4N_2O_2S$: 409).

Example 82

In analogy to example 1, on reaction of 5-(4-fluoro-2-methyl-phenyl)-pyridin-2-ylamine with 4-trifluoromethyl-benzenesulfonyl chloride there was obtained: N-[5-(4-Fluoro-2-methyl-phenyl)-pyridin-2-yl]-4-trifluoromethyl-benzenesulfonamide as a white solid. ISN mass spectrum, m/e: 409 (M−1 calculated for $C_{19}H_{14}F_4N_2O_2S$: 409).

Example 83

In analogy to example 1, on reaction of 5-(2-chloro-phenyl)-pyridin-2-ylamine with 3-trifluoromethyl-benzenesulfonyl chloride there was obtained: N-[5-(2-Chloro-phenyl)-pyridin-2-yl]-3-trifluoromethyl-benzenesulfonamide as a white solid. ISN mass spectrum, m/e: 411 (M−1 calculated for $C_{18}H_{12}ClF_3N_2O_3S$: 411).

Example 84

In analogy to example 1, on reaction of 5-(2-chloro-phenyl)-pyridin-2-ylamine with 4-ethyl-benzenesulfonyl chloride there was obtained: N-[5-(2-Chloro-phenyl)-pyridin-2-yl]-4-ethyl-benzenesulfonamide as a white solid. ISN mass spectrum, m/e: 371.1 (M−1 calculated for $C_{19}H_{17}ClN_2O_2S$: 371).

Example 85

In analogy to example 1, on reaction of 5-(2-chloro-phenyl)-pyridin-2-ylamine with 3-chloro-benzenesulfonyl chloride there was obtained: 3-Chloro-N-[5-(2-chloro-phenyl)-pyridin-2-yl]-benzenesulfonamide as white crystals. ISN mass spectrum, m/e: 377.1 (M−1 calculated for $C_{17}H_{12}Cl_2N_2O_3S$: 377).

Example 86

In analogy to example 1, on reaction of 5-(2,4-dichloro-phenyl)-pyridin-2-ylamine with 3-chloro-4-fluoro-benzenesulfonyl chloride there was obtained: 3-Chloro-N-[5-(2,4-dichloro-phenyl)-pyridin-2-yl]-4-fluoro-benzenesulfonamide as a crystalline white solid. ISN mass spectrum, m/e: 429.1 (M−1 calculated for $C_{17}H_{10}Cl_3FN_2O_2S$: 429).

Example 87

In analogy to example 1, on reaction of 5-(2,4-dichloro-phenyl)-pyridin-2-ylamine with 4-ethyl-benzenesulfonyl chloride there was obtained: N-[5-(2,4-Dichloro-phenyl)-pyridin-2-yl]-4-ethyl-benzenesulfonamide as a crystalline white solid. ISN mass spectrum, m/e: 405.1 (M−1 calculated for $C_{19}H_{16}Cl_2N_2O_2S$: 405).

Example 88

In analogy to example 1, on reaction of 5-(2,4-dichloro-phenyl)-pyridin-2-ylamine with 3-trifluoromethyl-benzenesulfonyl chloride there was obtained: N-[5-(2,4-Dichloro-phenyl)-pyridin-2-yl]-3-trifluoromethyl-benzenesulfonamide as an white foam. ISP mass spectrum, m/e: 444.9 (M−1 calculated for $C_{18}H_{11}Cl_2F_3N_2O_2S$: 445).

Example 89

In analogy to example 1, on reaction of 5-(2-chloro-phenyl)-6-methyl-pyridin-2-ylamine with 3-trifluoromethyl-benzenesulfonyl chloride there was obtained: N-[5-(2-Chloro-phenyl)-6-methyl-pyridin-2-yl]-3-trifluoromethyl-benzenesulfonamide as a white foam. ISN mass spectrum, m/e: 425 (M−1 calculated for $C_{19}H_{14}ClF_3N_2O_2S$: 425).

Example 90

In analogy to example 1, on reaction of 5-(2-chloro-phenyl)-6-methyl-pyridin-2-ylamine with 4-trifluoromethoxy-benzenesulfonyl chloride there was obtained: N-[5-(2-Chloro-phenyl)-6-methyl-pyridin-2-yl]-4-trifluoromethoxy-benzenesulfonamide as a white foam. ISN mass spectrum, m/e: 441.1 (M−1 calculated for $C_{19}H_{14}ClF_3N_2O_3S$: 441).

Example 91

In analogy to example 1, on reaction of 5-(2-chloro-phenyl)-pyridin-2-ylamine with 4-fluoro-benzenesulfonyl chloride there was obtained: N-[5-(2-Chloro-phenyl)-pyridin-2-yl]-4-fluoro-benzenesulfonamide as a white solid. ISN mass spectrum, m/e: 361 (M−1 calculated for $C_{17}H_{12}ClFN_2O_2S$: 361).

Example 92

In analogy to example 1, on reaction of 5-(2-chloro-phenyl)-pyridin-2-ylamine with 2,4-difluoro-benzenesulfonyl chloride there was obtained: N-[5-(2-Chloro-phenyl)-pyridin-2-yl]-2,4-difluoro-benzenesulfonamide as a white solid. ISN mass spectrum, m/e: 379 (M−1 calculated for $C_{17}H_{11}ClF_2N_2O_2S$: 379).

Example 93

In analogy to example 1, on reaction of 5-(2-chloro-phenyl)-pyridin-2-ylamine with 4-chloro-2,5-dimethyl-benzenesulfonyl chloride there was obtained: 4-Chloro-N-[5-(2-chloro-phenyl)-pyridin-2-yl]-2,5-dimethyl-benzenesulfonamide as a white solid. ISN mass spectrum, m/e: 405.1 (M−1 calculated for $C_{19}H_{16}Cl_2N_2O_2S$: 405).

Example 94

In analogy to example 1, on reaction of 5-(2-chloro-phenyl)-6-methyl-pyridin-2-ylamine with 4-chloro-2,5-dimethyl-benzenesulfonyl chloride there was obtained: 4-Chloro-N-[5-(2-chloro-phenyl)-6-methyl-pyridin-2-yl]-2,5-dimethyl-benzenesulfonamide as an off-white solid. ISN mass spectrum, m/e: 419 (M−1 calculated for $C_{20}H_{18}Cl_2N_2O_2S$: 419).

Example 95

In analogy to example 1, on reaction of 5-(2-chloro-phenyl)-6-methyl-pyridin-2-ylamine with 2,4-difluoro-benzenesulfonyl chloride there was obtained: N-[5-(2-Chloro-phenyl)-6-methyl-pyridin-2-yl]-2,4-difluoro-benzenesulfonamide as an off-white solid. ISN mass spectrum, m/e: 392.9 (M+1 calculated for $C_{18}H_{13}ClF_2N_2O_2S$: 393).

Example 96

In analogy to example 1, on reaction of 5-(2-chloro-phenyl)-6-methyl-pyridin-2-ylamine with 3,5-dichloro-benzenesulfonyl chloride there was obtained: 3,5-Dichloro-N-[5-(2-chloro-phenyl)-6-methyl-pyridin-2-yl]-benzenesulfonamide as an off-white solid. ISN mass spectrum, m/e: 425 (M−1 calculated for $C_{18}H_{13}Cl_3N_2O_2S$: 425).

Example 97

In analogy to example 1, on reaction of 5-(2,4-chloro-phenyl)-6-methyl-pyridin-2-ylamine with 3-trifluoromethyl-benzenesulfonyl chloride there was obtained: N-[5-(2,4-Dichloro-phenyl)-6-methyl-pyridin-2-yl]-3-trifluoromethyl-benzenesulfonamide as an colourless waxy solid. ISN mass spectrum, m/e: 459 (M−1 calculated for $C_{19}H_{13}Cl_2F_3N_2O_2S$: 459).
Preparation of the Starting Material:
In analogy to example 1b), on reaction of 5-bromo-6-methyl-pyridin-2-ylamine with 2,4-dichloro-phenylboronic acid there was obtained: of 5-(2,4-chloro-phenyl)-6-methyl-pyridin-2-ylamine as a brown crystalline solid. ISP mass spectrum, m/e: 253 (M+1 calculated for $C_{12}H_{10}Cl2N_2$: 253).

Example 98

In analogy to example 1, on reaction of 5-(2,4-chloro-phenyl)-6-methyl-pyridin-2-ylamine with 4-fluoro-benzenesulfonyl chloride there was obtained: N-[5-(2,4-Dichloro-phenyl)-6-methyl-pyridin-2-yl]-4-fluoro-benzenesulfonamide as a colorless waxy solid. ISn mass spectrum, m/e: 409 (M−1 calculated for $C_{18}H_{13}Cl_2FN_2O_2S$: 409).

Example 99

In analogy to example 1, on reaction of 5-(2,4-chloro-phenyl)-6-methyl-pyridin-2-ylamine with 2,4-difluoro-benzenesulfonyl chloride there was obtained: N-[5-(2,4-Dichloro-phenyl)-6-methyl-pyridin-2-yl]-2,4-difluoro-benzenesulfonamide as a colorless foam. ISN mass spectrum, m/e: 427.1 (M−1 calculated for $C_{18}H_{12}Cl_2F_2N_2O_2S$: 427).

Example 100

In analogy to example 1, on reaction of 5-(2,4-chloro-phenyl)-6-methyl-pyridin-2-ylamine with 4-chloro-2,5-dimethyl-benzenesulfonyl chloride there was obtained: 4-Chloro-N-[5-(2,4-dichloro-phenyl)-6-methyl-pyridin-2-yl]-2,5-dimethyl-benzenesulfonamide as a white powder. ISN mass spectrum, m/e: 453.1 (M−1 calculated for $C_{20}H_{17}Cl_3N_2O_2S$: 453).

Example 101

In analogy to example 1, on reaction of 5-(2,4-dichloro-phenyl)-pyridin-2-ylamine with 2,4-dichloro-6-methyl-benzenesulfonyl chloride there was obtained: 2,4-Dichloro-N-[5-(2,4-dichloro-phenyl)-pyridin-2-yl]-6-methyl-benzenesulfonamide as a white foam. ISN mass spectrum, m/e: 458.9 (M−1 calculated for $C_{18}H_{12}Cl_4N_2O_2S$: 458).

Example 102

In analogy to example 1, on reaction of 5-(2,4-dichloro-phenyl)-pyridin-2-ylamine with 3-chloro-benzenesulfonyl chloride there was obtained: 3-Chloro-N-[5-(2,4-dichloro-phenyl)-pyridin-2-yl]-benzenesulfonamide as an off-white foam. ISN mass spectrum, m/e: 411 (M−1 calculated for $C_{17}H_{11}Cl_3N_2O_2S$: 411).

Example 103

In analogy to example 1, on reaction of 5-(2,4-dichloro-phenyl)-pyridin-2-ylamine with 4-chloro-benzenesulfonyl chloride there was obtained: 4-Chloro-N-[5-(2,4-dichloro-phenyl)-pyridin-2-yl]-benzenesulfonamide as an off-white foam. ISP mass spectrum, m/e: 411 (M−1 calculated for $C_{17}H_{11}Cl_3N_2O_2S$: 411).

Example 104

In analogy to example 1, on reaction of 5-(2-chloro-phenyl)-6-methyl-pyridin-2-ylamine with 3-fluoro-benzenesulfonyl chloride there was obtained: N-[5-(2-Chloro-phenyl)-6-methyl-pyridin-2-yl]-3-fluoro-benzenesulfonamide as an light-yellow foam. ISN mass spectrum, m/e: 375.2 (M−1 calculated for $C_{18}H_{14}ClFN_2O_2S$: 375).

Example 105

In analogy to example 1, on reaction of 5-(2-chloro-phenyl)-6-methyl-pyridin-2-ylamine with 3-chloro-benzenesulfonyl chloride there was obtained: 3-Chloro-N-[5-(2-chloro-phenyl)-6-methyl-pyridin-2-yl]-benzenesulfonamide as a light-yellow foam. ISN mass spectrum, m/e: 391 (M−1 calculated for $C_{18}H_{14}Cl_2N_2O_2S$: 391).

Example 106

In analogy to example 1, on reaction of 5-(2-chloro-phenyl)-6-methyl-pyridin-2-ylamine with 2,4-dichloro-benzenesulfonyl chloride there was obtained: 2,4-Dichloro-N-[5-(2-chloro-phenyl)-6-methyl-pyridin-2-yl]-benzenesulfonamide as a light-yellow foam. ISN mass spectrum, m/e: 424.9 (M−1 calculated for $C_{18}H_{13}Cl_3N_2O_2S$: 425).

Example 107

In analogy to example 1, on reaction of 5-(2-chloro-phenyl)-6-methyl-pyridin-2-ylamine with 2,4-dichloro-5-methyl-benzenesulfonyl chloride there was obtained: 2,4-Dichloro-N-[5-(2-chloro-phenyl)-6-methyl-pyridin-2-yl]-5-methyl-benzenesulfonamide as a light-yellow foam. ISN mass spectrum, m/e: 439 (M−1 calculated for $C_{19}H_{15}Cl_3N_2O_2S$: 439).

Example 108

In analogy to example 1, on reaction of 5-(4-fluoro-2-methyl-phenyl)-6-methyl-pyridin-2-ylamine with 3-trifluomethyl-benzenesulfonyl chloride there was obtained: N-[5-(4-Fluoro-2-methyl-phenyl)-6-methyl-pyridin-2-yl]-3-trifluoromethyl-benzenesulfonamide as a light-yellow foam. ISN mass spectrum, m/e: 423 (M−1 calculated for $C_{20}H_{16}F_4N_2O_2S$: 423).

Example 109

In analogy to example 1, on reaction of 5-(4-fluoro-2-methyl-phenyl)-6-methyl-pyridin-2-ylamine with 2,4-dichloro-6-methyl-benzenesulfonyl chloride there was obtained: 2,4-Dichloro-N-[5-(4-fluoro-2-methyl-phenyl)-6-methyl-pyridin-2-yl]-6-methyl-benzenesulfonamide as a light-yellow foam. ISN mass spectrum, m/e: 437.2 (M−1 calculated for $C_{20}H_{17}Cl_2FN_2O_2S$: 437).

Example 110

In analogy to example 1, on reaction of 5-(4-fluoro-2-methyl-phenyl)-6-methyl-pyridin-2-ylamine with 3-chloro-benzenesulfonyl chloride there was obtained: 3-Chloro-N-[5-(4-fluoro-2-methyl-phenyl)-6-methyl-pyridin-2-yl]-benzenesulfonamide as a light-yellow foam. ISN mass spectrum, m/e: 389 (M−1 calculated for $C_{19}H_{16}ClFN_2O_2S$: 389).

Example 111

In analogy to example 1, on reaction of 5-(4-fluoro-2-methyl-phenyl)-6-methyl-pyridin-2-ylamine with 4-chloro-benzenesulfonyl chloride there was obtained: 4-Chloro-N-[5-(4-fluoro-2-methyl-phenyl)-6-methyl-pyridin-2-yl]-benzenesulfonamide as a light-yellow foam. ISN mass spectrum, m/e: 389.1 (M−1 calculated for $C_{19}H_{16}ClFN_2O_2S$: 389).

Example 112

In analogy to example 1, on reaction of 5-(4-fluoro-2-methyl-phenyl)-6-methyl-pyridin-2-ylamine with 4-trifluoromethoxy-benzenesulfonyl chloride there was obtained: N-[5-(4-Fluoro-2-methyl-phenyl)-6-methyl-pyridin-2-yl]-4-trifluoromethoxy-benzenesulfonamide as a light-brown viscous oil. ISN mass spectrum, m/e: 439.1 (M−1 calculated for $C_{20}H_{16}F_4N_2O_3S$: 439).

Example 113

In analogy to example 1, on reaction of 5-(4-fluoro-2-methyl-phenyl)-6-methyl-pyridin-2-ylamine with 3-methyl-benzenesulfonyl chloride there was obtained: N-[5-(4-Fluoro-2-methyl-phenyl)-6-methyl-pyridin-2-yl]-3-methyl-benzenesulfonamide as a light-yellow viscous oil. ISN mass spectrum, m/e: 369 (M−1 calculated for $C_{20}H_{19}FN_2O_2S$: 369).

Example 114

In analogy to example 1, on reaction of 5-(4-fluoro-2-methyl-phenyl)-6-methyl-pyridin-2-ylamine with 2-chloro-5-trifluoromethyl-benzenesulfonyl chloride there was obtained: 2-Chloro-N-[5-(4-fluoro-2-methyl-phenyl)-6-methyl-pyridin-2-yl]-5-trifluoromethyl-benzenesulfonamide as a light-yellow viscous oil. ISN mass spectrum, m/e: 457.1 (M−1 calculated for $C_{20}H_{15}ClF_4N_2O_2S$: 457).

Example 115

In analogy to example 1, on reaction of 5-(4-fluoro-2-methyl-phenyl)-6-methyl-pyridin-2-ylamine with 4-fluoro-3-trifluoromethyl-benzenesulfonyl chloride there was obtained: 2-Chloro-N-[5-(4-fluoro-2-methyl-phenyl)-6-methyl-pyridin-2-yl]-5-trifluoromethyl-benzenesulfonamide as a light-brown viscous oil. ISN mass spectrum, m/e: 441.1 (M−1 calculated for $C_{20}H_{15}F_5N_2O_2S$: 441).

Example 116

In analogy to example 1, on reaction of 5-(2-chloro-phenyl)-6-methyl-pyridin-2-ylamine with 3-methyl-benzenesulfonyl chloride there was obtained: N-[5-(2-Chloro-phenyl)-6-methyl-pyridin-2-yl]-3-methyl-benzenesulfonamide as a light-yellow viscous oil. ISN mass spectrum, m/e: 371.2 (M−1 calculated for $C_{19}H_{17}ClN_2O_2S$: 371).

Example 117

In analogy to example 1, on reaction of 5-(2-chloro-phenyl)-6-methyl-pyridin-2-ylamine with 3-chloro-4-fluoro-benzenesulfonyl chloride there was obtained: 3-Chloro-N-(2-chloro-phenyl)-6-methyl-pyridin-2-yl]-4-fluoro-benzenesulfonamide as a light-yellow viscous oil. ISN mass spectrum, m/e: 409.3 (M−1 calculated for $C_{18}H_{13}Cl_2FN_2O_2S$: 409).

Example 118

In analogy to example 1, on reaction of 5-(2-chloro-phenyl)-6-methyl-pyridin-2-ylamine with 3-chloro-5-trifluoromethyl-benzenesulfonyl chloride there was obtained: 2-Chloro-N-[5-(2-chloro-phenyl)-6-methyl-pyridin-2-yl]-5-trifluoromethyl-benzenesulfonamide as a light-yellow viscous oil. ISN mass spectrum, m/e: 459.2 (M−1 calculated for $C_{19}H_{13}Cl_2F_3N_2O_2S$: 459).

Example 119

In analogy to example 1, on reaction of 5-(2-chloro-phenyl)-6-methyl-pyridin-2-ylamine with 4-fluoro-3-trifluoromethyl-benzenesulfonyl chloride there was obtained: N-[5-(2-Chloro-phenyl)-6-methyl-pyridin-2-yl]-4-fluoro-3-trifluoromethyl-benzenesulfonamide as a light-brown viscous oil. ISN mass spectrum, m/e: 442.9 (M−1 calculated for $C_{19}H_{13}ClF_4N_2O_2S$: 443).

Example 120

In analogy to example 1, on reaction of 5-(2,3-dichloro-phenyl)-pyridin-2-ylamine with 3-fluoro-4-methyl-benzenesulfonyl chloride there was obtained: N-[5-(2,3-Dichloro-phenyl)-pyridin-2-yl]-3-fluoro-4-methyl-benzenesulfonamide as a colorless solid. ISN mass spectrum, m/e: 409.1 (M−1 calculated for $C_{18}H_{13}Cl_2N_2O_2S$: 409).

Example 121

In analogy to example 1, on reaction of 5-(2,3-dichloro-phenyl)-pyridin-2-ylamine with 3,5-dimethyl-benzenesulfonyl chloride there was obtained: N-[5-(2,3-Dichloro-phenyl)-pyridin-2-yl]-3,5-dimethyl-benzenesulfonamide as a white solid. ISN mass spectrum, m/e: 405.1 (M−1 calculated for $C_{19}H_{16}Cl_2N_2O_2S$: 405).

Example 122

In analogy to example 1, on reaction of 5-(5-fluoro-2-methyl-phenyl)-pyridin-2-ylamine with 3-trifluoromethyl-benzenesulfonyl chloride there was obtained: N-[5-(5-Fluoro-2-methyl-phenyl)-pyridin-2-yl]-3-trifluoromethyl-benzenesulfonamide as a white solid. ISN mass spectrum, m/e: 409.1 (M−1 calculated for $C_{19}H_{14}F_4N_2O_2S$: 409).
Preparation of the Starting Material:

In analogy to example 1b), on reaction of 5-bromo-pyridin-2-ylamine with 5-fluoro-2-methyl-phenylboronic acid there was obtained: 5-(5-fluoro-2-methyl-phenyl)-pyridin-2-

Example 123

In analogy to example 1, on reaction of 5-(5-fluoro-2-methyl-phenyl)-pyridin-2-ylamine with 4-fluoro-benzenesulfonyl chloride there was obtained: 4-Fluoro-N-[5-(5-fluoro-2-methyl-phenyl)-pyridin-2-yl]-benzenesulfonamide as a white solid. ISN mass spectrum, m/e: 359 (M−1 calculated for $C_{18}H_{14}F_2N_2O_2S$: 359).

Example 124

In analogy to example 1, on reaction of 5-(5-fluoro-2-methyl-phenyl)-pyridin-2-ylamine with 3-chloro-2-methyl-benzenesulfonyl chloride there was obtained: 3-Chloro-N-[5-(5-fluoro-2-methyl-phenyl)-pyridin-2-yl]-2-methyl-benzenesulfonamide as a white solid. ISN mass spectrum, m/e: 389.1 (M−1 calculated for $C_{19}H_{16}ClFN_2O_2S$: 389).

Example 125

In analogy to example 1, on reaction of 5-(5-chloro-2-methyl-phenyl)-pyridin-2-ylamine with 3-trifluoromethyl-benzenesulfonyl chloride there was obtained: N-[5-(5-Chloro-2-methyl-phenyl)-pyridin-2-yl]-3-trifluoromethyl-benzenesulfonamide as an off-white solid. ISN mass spectrum, m/e: 425.1 (M−1 calculated for $C_{19}H_{14}ClF_3N_2O_2S$: 425).
Preparation of the Starting Material:
In analogy to example 1b), on reaction of 5-bromo-pyridin-2-ylamine with 5-chloro-2-methyl-phenylboronic acid there was obtained: 5-(5-chloro-2-methyl-phenyl)-pyridin-2-ylamine as a white solid. EI mass spectrum, m/e: 218.1 (M calculated for $C_{12}H_{11}ClN_2$: 218).

Example 126

In analogy to example 1, on reaction of 5-(5-chloro-2-methyl-phenyl)-pyridin-2-ylamine with 4-fluoro-benzenesulfonyl chloride there was obtained: N-[5-(5-Chloro-2-methyl-phenyl)-pyridin-2-yl]-4-fluoro-benzenesulfonamide as a light-yellow solid. ISN mass spectrum, m/e: 375.2 (M−1 calculated for $C_{18}H_{14}ClFN_2O_2S$: 375).

Example 127

In analogy to example 1, on reaction of 5-(5-chloro-2-methyl-phenyl)-pyridin-2-ylamine with 3-chloro-2-methyl-benzenesulfonyl chloride there was obtained: 3-Chloro-N-[5-(5-chloro-2-methyl-phenyl)-pyridin-2-yl]-2-methyl-benzenesulfonamide as a white solid. ISN mass spectrum, m/e: 405.1 (M−1 calculated for $C_{19}H_{16}Cl_2N_2O_2S$: 405).

Example 128

In analogy to example 1, on reaction of 5-(6-Chloro-2-fluoro-3-methyl-phenyl)-pyridin-2-ylamine with 3-chloro-2-methyl-benzenesulfonyl chloride there was obtained: 3-Chloro-N-[5-(6-chloro-2-fluoro-3-methyl-phenyl)-pyridin-2-yl]-2-methyl-benzenesulfonamide as a white solid. ISn mass spectrum, m/e: 422.9 (M−1 calculated for $C_{19}H_{15}Cl_2FN_2O_2S$: 423).
Preparation of the Starting Material:
In analogy to example 1b), on reaction of 5-bromo-pyridin-2-ylamine with 6-Chloro-2-fluoro-3-methyl-phenylboronic acid there was obtained: 5-(5-chloro-2-methyl-phenyl)-pyridin-2-ylamine as a white solid. EI mass spectrum, m/e: 237.1 (M calculated for $C_{12}H_{10}ClFN_2$: 237).

Example 129

In analogy to example 1, on reaction of 5-(6-Chloro-2-fluoro-3-methyl-phenyl)-pyridin-2-ylamine with 3-trifluoromethyl-benzenesulfonyl chloride there was obtained: N-[5-(6-Chloro-2-fluoro-3-methyl-phenyl)-pyridin-2-yl]-3-trifluoromethyl-benzenesulfonamide as a light-yellow solid. ISN mass spectrum, m/e: 443.2 (M−1 calculated for $C_{19}H_{13}ClF_4N_2O_2S$: 443).

Example 130

In analogy to example 1, on reaction of 5-(6-Chloro-2-fluoro-3-methyl-phenyl)-pyridin-2-ylamine with 4-fluoro-benzenesulfonyl chloride there was obtained: N-[5-(6-Chloro-2-fluoro-3-methyl-phenyl)-pyridin-2-yl]-4-fluoro-benzenesulfonamide as a light-yellow solid. ISN mass spectrum, m/e: 393.1 (M−1 calculated for $C_{18}H_{13}ClF_2N_2O_2S$: 393).

Example 131

In analogy to example 1, on reaction of 5-(5-Chloro-2-methyl-phenyl)-6-methyl-pyridin-2-ylamine with 3-trifluoromethyl-benzenesulfonyl chloride there was obtained: N-[5-(5-Chloro-2-methyl-phenyl)-6-methyl-pyridin-2-yl]-3-trifluoromethyl-benzenesulfonamide as an orange oil. ISN mass spectrum, m/e: 439 (M−1 calculated for $C_{20}H_{16}ClF_3N_2O_2S$: 439).
Preparation of the Starting Material:
In analogy to example 1b), on reaction of 5-bromo-6-methyl-pyridin-2-ylamine with 5-chloro-2-methyl-phenylboronic acid there was obtained: 5-(5-Chloro-2-methyl-phenyl)-6-methyl-pyridin-2-ylamine as a white solid. ISP mass spectrum, m/e: 233 (M+1 calculated for $C_{13}H_{13}ClN_2$: 233).

Example 132

In analogy to example 1, on reaction of 5-(5-Chloro-2-methyl-phenyl)-6-methyl-pyridin-2-ylamine with 4-fluoro-benzenesulfonyl chloride there was obtained: N-[5-(5-Chloro-2-methyl-phenyl)-6-methyl-pyridin-2-yl]-4-fluoro-benzenesulfonamide as a white solid. ISN mass spectrum, m/e: 389 (M−1 calculated for $C_{19}H_{16}ClFN_2O_2S$: 389).

Example 133

In analogy to example 1, on reaction of 5-(5-Chloro-2-methyl-phenyl)-6-methyl-pyridin-2-ylamine with 3-chloro-2-methyl-benzenesulfonyl chloride there was obtained: 3-Chloro-N-[5-(5-chloro-2-methyl-phenyl)-6-methyl-pyridin-2-yl]-2-methyl-benzenesulfonamide as a white solid. ISN mass spectrum, m/e: 419 (M−1 calculated for $C_{20}H_{18}Cl2N_2O_2S$: 419).

Example 134

In analogy to example 1, on reaction of 5-(6-Chloro-2-fluoro-3-methyl-phenyl)-6-methyl-pyridin-2-ylamine with 3-trifluoromethyl-benzenesulfonyl chloride there was obtained: N-[5-(6-Chloro-2-fluoro-3-methyl-phenyl)-6-methyl-pyridin-2-yl]-3-trifluoromethyl-benzenesulfonamide as a light-yellow solid. ISN mass spectrum, m/e: 457.2 (M−1 calculated for $C_{20}H_{15}ClF_4N_2O_2S$: 457).

Preparation of the Starting Material

In analogy to example 1b), on reaction of 5-bromo-6-methyl-pyridin-2-ylamine with 6-Chloro-2-fluoro-3-methyl-phenylboronic acid there was obtained: 5-(5-chloro-2-methyl-phenyl)-6-methyl-pyridin-2-ylamine as which was used without further purification in the next reaction step.

Example 135

In analogy to example 1, on reaction of 5-(6-Chloro-2-fluoro-3-methyl-phenyl)-6-methyl-pyridin-2-ylamine with 4-fluoro-benzenesulfonyl chloride there was obtained: N-[5-(6-Chloro-2-fluoro-3-methyl-phenyl)-6-methyl-pyridin-2-yl]-4-fluoro-benzenesulfonamide as an off-white solid. ISN mass spectrum, m/e: 407.2 (M−1 calculated for $C_{19}H_{15}ClFN_2O_2S$: 407).

Example 136

In analogy to example 1, on reaction of 5-(4-fluoro-2-methyl-phenyl)-pyridin-2-ylamine with 4-chloro-benzenesulfonyl chloride there was obtained: 4-Chloro-N-[5-(4-fluoro-2-methyl-phenyl)-pyridin-2-yl]-benzenesulfonamide as a white solid. ISN mass spectrum, m/e: 375.2 (M−1 calculated for $C_{18}H_{14}ClFN_2O_2S$: 375).

Example 137

In analogy to example 1, on reaction of 5-(4-fluoro-2-methyl-phenyl)-pyridin-2-ylamine with 3-chloro-benzenesulfonyl chloride there was obtained: 3-Chloro-N-[5-(4-fluoro-2-methyl-phenyl)-pyridin-2-yl]-benzenesulfonamide as a white solid. ISN mass spectrum, m/e: 375.2 (M−1 calculated for $C_{18}H_{14}ClFN_2O_2S$: 375).

Example 138

In analogy to example 1, on reaction of 5-(4-fluoro-2-methyl-phenyl)-pyridin-2-ylamine with 2,4-dichloro-5-methyl-benzenesulfonyl chloride there was obtained: 2,4-Dichloro-N-[5-(4-fluoro-2-methyl-phenyl)-pyridin-2-yl]-6-methyl-benzenesulfonamide as a white solid. ISN mass spectrum, m/e: 422.9 (M−1 calculated for $C_{19}H_{15}Cl_2FN_2O_2S$: 423).

Example 139

In analogy to example 1, on reaction of 5-(2,5-Dichloro-phenyl)-6-methyl-pyridin-2-ylamine with 3-chloro-benzenesulfonyl chloride there was obtained: 3-Chloro-N-[5-(2,5-dichloro-phenyl)-6-methyl-pyridin-2-yl]-benzenesulfonamide as a light-yellow solid. ISN mass spectrum, m/e: 425 (M−1 calculated for $C_{18}H_{13}Cl_3N_2O_2S$: 425).

Preparation of the Starting Material:

In analogy to example 1b), on reaction of 5-bromo-6-methyl-pyridin-2-ylamine with 2,5-dichloro-phenylboronic acid there was obtained: 5-(2,5-Dichloro-phenyl)-6-methyl-pyridin-2-ylamine as white solid. EI mass spectrum, m/e: 252.1 (M calculated for $C_{12}H_{10}Cl_2N_2$: 252).

Example 140

In analogy to example 1, on reaction of 5-(2,5-Dichloro-phenyl)-6-methyl-pyridin-2-ylamine with 4-fluoro-benzenesulfonyl chloride there was obtained: N-[5-(2,5-Dichloro-phenyl)-6-methyl-pyridin-2-yl]-4-fluoro-benzenesulfonamide as a white solid. ISN mass spectrum, m/e: 409 (M−1 calculated for $C_{18}H_{13}Cl_2FN_2O_2S$: 409).

Example 141

In analogy to example 1, on reaction of 5-(5-Fluoro-2-methyl-phenyl)-6-methyl-pyridin-2-ylamine with 3-trifluoro-benzenesulfonyl chloride there was obtained: N-[5-(5-Fluoro-2-methyl-phenyl)-6-methyl-pyridin-2-yl]-3-trifluoromethyl-benzenesulfonamide as an off-white solid. ISN mass spectrum, m/e: 422.9 (M−1 calculated for $C_{20}H_{16}F_4N_2O_2S$: 423).

Preparation of the Starting Material:

In analogy to example 1b), on reaction of 5-bromo-6-methyl-pyridin-2-ylamine with 5-fluoro-2-methyl-phenylboronic acid there was obtained: 5-(5-Fluoro-2-methyl-phenyl)-6-methyl-pyridin-2-ylamine a light-yellow oil. EI mass spectrum, m/e: 216.2 (M calculated for $C_{13}H_{13}FN_2$: 216).

Example 142

In analogy to example 1, on reaction of 5-(5-Fluoro-2-methyl-phenyl)-6-methyl-pyridin-2-ylamine with 4-fluoro-benzenesulfonyl chloride there was obtained: 4-Fluoro-N-[5-(5-fluoro-2-methyl-phenyl)-6-methyl-pyridin-2-yl]-benzenesulfonamide as an off-white solid. ISN mass spectrum, m/e: 373.1 (M−1 calculated for $C_{19}H_{16}F_2N_2O_2S$: 373).

Example 143

In analogy to example 1, on reaction of 5-(5-Fluoro-2-methyl-phenyl)-6-methyl-pyridin-2-ylamine with 3-chloro-benzenesulfonyl chloride there was obtained: 3-Chloro-N-[5-(5-fluoro-2-methyl-phenyl)-6-methyl-pyridin-2-yl]-benzenesulfonamide as an off-white solid. ISN mass spectrum, m/e: 389 (M−1 calculated for $C_{19}H_{16}ClFN_2O_2S$: 389).

Example 144

In analogy to example 1, on reaction of 5-(2,5-Dichloro-phenyl)-6-methyl-pyridin-2-ylamine with 3-trifluoromethyl-benzenesulfonyl chloride there was obtained: N-[5-(2,5-Dichloro-phenyl)-6-methyl-pyridin-2-yl]-3-trifluoromethyl-benzenesulfonamide as an orange oil. ISN mass spectrum, m/e: 459 (M−1 calculated for $C_{19}H_{13}Cl_2F_3N_2O_2S$: 459).

Example 145

In analogy to example 1, on reaction of 5-(2-Chloro-4-fluoro-phenyl)-6-methyl-pyridin-2-ylamine with 3-trifluoro-benzenesulfonyl chloride there was obtained: N-[5-(2-Chloro-4-fluoro-phenyl)-6-methyl-pyridin-2-yl]-3-trifluoromethyl-benzenesulfonamide as an light-yellow solid. ISN mass spectrum, m/e: 442.9 (M−1 calculated for $C_{19}H_{13}ClF_4N_2O_2S$: 443).

Preparation of the Starting Material:

In analogy to example 1b), on reaction of 5-bromo-6-methyl-pyridin-2-ylamine with 2-chloro-4-fluoro-phenylboronic acid there was obtained: 5-(2-Chloro-4-fluoro-phenyl)-6-methyl-pyridin-2-ylamine an off-white solid. EI mass spectrum, m/e: 236.1 (M calculated for $C_{12}H_{10}ClFN_2$: 236).

Example 146

In analogy to example 1, on reaction of 5-(2-Chloro-4-fluoro-phenyl)-6-methyl-pyridin-2-ylamine with 4-fluorobenzenesulfonyl chloride there was obtained: N-[5-(2-Chloro-4-fluoro-phenyl)-6-methyl-pyridin-2-yl]-4-fluoro-benzenesulfonamide as a white solid. ISN mass spectrum, m/e: 392.9 (M−1 calculated for $C_{18}H_{13}ClF_2N_2O_2S$: 393).

Example 147

In analogy to example 1, on reaction of 5-(2-Chloro-4-fluoro-phenyl)-6-methyl-pyridin-2-ylamine with 3-chloro-benzenesulfonyl chloride there was obtained: 3-Chloro-N-[5-(2-chloro-4-fluoro-phenyl)-6-methyl-pyridin-2-yl]-benzenesulfonamide as a white solid. ISN mass spectrum, m/e: 409 (M−1 calculated for $C_{18}H_{13}Cl_2FN_2O_2S$: 409).

Example 148

In analogy to example 1, on reaction of 5-(2,3-Dichloro-phenyl)-6-methyl-pyridin-2-ylamine with 3-trifluoro-benzenesulfonyl chloride there was obtained: N-[5-(2,3-Dichloro-phenyl)-6-methyl-pyridin-2-yl]-3-trifluoromethyl-benzenesulfonamide as a light-yellow amorphous solid. ISN mass spectrum, m/e: 459.2 (M−1 calculated for $C_{19}H_{13}Cl_2F_3N_2O_2S$: 459).
Preparation of the Starting Material:

In analogy to example 1b), on reaction of 5-bromo-6-methyl-pyridin-2-ylamine with 2,3-dichloro-phenylboronic acid there was obtained: 5-(2,3-Dichloro-phenyl)-6-methyl-pyridin-2-ylamine an off-white solid. EI mass spectrum, m/e: 252.1 (M calculated for $C_{12}H_{10}Cl_2N_2$: 252).

Example 149

In analogy to example 1, on reaction of 5-(2,3-Dichloro-phenyl)-6-methyl-pyridin-2-ylamine with 4-fluoro-benzenesulfonyl chloride there was obtained: N-[5-(2,3-Dichloro-phenyl)-6-methyl-pyridin-2-yl]-4-fluoro-benzenesulfonamide as a white solid. ISN mass spectrum, m/e: 409.3 (M−1 calculated for $C_{18}H_{13}Cl_2FN_2O_2S$: 409).

Example 150

In analogy to example 1, on reaction of 5-(2,3-Dichloro-phenyl)-6-methyl-pyridin-2-ylamine with 3-chloro-benzenesulfonyl chloride there was obtained: 3-Chloro-N-[5-(2,3-dichloro-phenyl)-6-methyl-pyridin-2-yl]-benzenesulfonamide as a white foam. ISN mass spectrum, m/e: 425.1 (M−1 calculated for $C_{18}H_{13}Cl_3N_2O_2S$: 425).

Example 151

In analogy to example 1, on reaction of 5-(2,3-Dichloro-phenyl)-6-methyl-pyridin-2-ylamine with 2,4-dichloro-6-methyl-benzenesulfonyl chloride there was obtained: 2,4-Dichloro-N-[5-(2,3-dichloro-phenyl)-6-methyl-pyridin-2-yl]-6-methyl-benzenesulfonamide as an off-white foam. ISN mass spectrum, m/e: 473.1 (M−1 calculated for $C_{19}H_{14}Cl_4N_2O_2S$: 473).

Example 152

In analogy to example 1, on reaction of 5-(2,3-Dichloro-phenyl)-6-methyl-pyridin-2-ylamine with 3-methyl-benzenesulfonyl chloride there was obtained: N-[5-(2,3-Dichloro-phenyl)-6-methyl-pyridin-2-yl]-3-methyl-benzenesulfonamide as a white foam. ISN mass spectrum, m/e: 405.3 (M−1 calculated for $C_{19}H_{16}Cl_2N_2O_2S$: 405).

Example 153

In analogy to example 1, on reaction of 5-(2,5-Dichloro-phenyl)-6-methyl-pyridin-2-ylamine with 2,4-dichloro-6-methyl-benzenesulfonyl chloride there was obtained: 2,4-Dichloro-N-[5-(2,5-dichloro-phenyl)-6-methyl-pyridin-2-yl]-6-methyl-benzenesulfonamide as a light-yellow foam. ISN mass spectrum, m/e: 475 (M−1 calculated for $C_{19}H_{14}Cl_4F_3N_2O_2S$: 475).

Example 154

In analogy to example 1, on reaction of 5-(2-Chloro-4-fluoro-phenyl)-6-methyl-pyridin-2-ylamine with 3-methyl-benzenesulfonyl chloride there was obtained: N-[5-(2-Chloro-4-fluoro-phenyl)-6-methyl-pyridin-2-yl]-3-methyl-benzenesulfonamide as a white foam. ISN mass spectrum, m/e: 389 (M−1 calculated for $C_{19}H_{16}ClFN_2O_2S$: 389).

Example 155

In analogy to example 1, on reaction of 5-(2-Chloro-4-fluoro-phenyl)-6-methyl-pyridin-2-ylamine with 2,4-dichloro-5-methyl-benzenesulfonyl chloride there was obtained: 2,4-Dichloro-N-[5-(2-chloro-4-fluoro-phenyl)-6-methyl-pyridin-2-yl]-6-methyl-benzenesulfonamide as a white foam. ISN mass spectrum, m/e: 457.1 (M−1 calculated for $C_{19}H_{14}Cl_3FN_2O_2S$: 457).

Example 156

In analogy to example 1, on reaction of 5-(2,4-bis-trifluoromethyl-phenyl)-pyridin-2-ylamine with 3-chloro-benzenesulfonyl chloride there was obtained: N-[5-(2,4-Bis-trifluoromethyl-phenyl)-pyridin-2-yl]-3-chloro-benzenesulfonamide as a white solid. ISN mass spectrum, m/e: 479 (M−1 calculated for $C_{19}H_{11}ClF_6N_2O_2S$: 479).

Example 157

In analogy to example 1, on reaction of 5-(2,4-bis-trifluoromethyl-phenyl)-pyridin-2-ylamine with 3-methyl-benzenesulfonyl chloride there was obtained: N-[5-(2,4-Bis-trifluoromethyl-phenyl)-pyridin-2-yl]-3-methyl-benzenesulfonamide as a white solid. ISN mass spectrum, m/e: 459.1 (M−1 calculated for $C_{20}H_{14}F_6N_2O_2S$: 459).

Example 158

In analogy to example 1, on reaction of 5-(2,4-bis-trifluoromethyl-phenyl)-pyridin-2-ylamine with 4-fluoro-benzenesulfonyl chloride there was obtained: N-[5-(2,4-Bis-trifluoromethyl-phenyl)-pyridin-2-yl]-4-fluoro-benzenesulfonamide as a white foam. ISN mass spectrum, m/e: 463 (M−1 calculated for $C_{20}H_{11}F_7N_2O_2S$: 463).

Example 159

In analogy to example 1, on reaction of 5-(2,3-Dichloro-phenyl)-6-methyl-pyridin-2-ylamine with 4-fluoro-3-trifluoro-benzenesulfonyl chloride there was obtained: N-[5-(2,3-Dichloro-phenyl)-6-methyl-pyridin-2-yl]-4-fluoro-3-trifluoromethyl-benzenesulfonamide as an off-white foam. ISN mass spectrum, m/e: 476.9 (M−1 calculated for $C_{19}H_{12}Cl_2F_4N_2O_2S$: 477).

Example 160

In analogy to example 1, on reaction of 5-(2,3-Dichloro-phenyl)-6-methyl-pyridin-2-ylamine with 3-chloro-4-fluorobenzenesulfonyl chloride there was obtained: 3-Chloro-N-[5-(2,3-dichloro-phenyl)-6-methyl-pyridin-2-yl]-4-fluoro-benzenesulfonamide as an off-white foam. ISN mass spectrum, m/e: 442.9 (M−1 calculated for $C_{18}H_{12}Cl_3FN_2O_2S$: 443).

Example 161

In analogy to example 1, on reaction of 5-(2-Fluoro-phenyl)-6-methyl-pyridin-2-ylamine with 3-chloro-benzenesulfonyl chloride there was obtained: 3-Chloro-N-[5-(2-fluoro-phenyl)-6-methyl-pyridin-2-yl]-benzenesulfonamide as an off-white foam. ISN mass spectrum, m/e: 375.2 (M−1 calculated for $C_{18}H_{14}ClFN_2O_2S$: 375).
Preparation of the Starting Material:
In analogy to example 1b), on reaction of 5-bromo-6-methyl-pyridin-2-ylamine with 2-fluoro-phenylboronic acid there was obtained: -(2-Fluoro-phenyl)-6-methyl-pyridin-2-ylamine an off-white solid. EI mass spectrum, m/e: 202.2 (M calculated for $C_{12}H_{11}FN_2$: 202).

Example 162

In analogy to example 1, on reaction of 5-(2-Fluoro-phenyl)-6-methyl-pyridin-2-ylamine with 4-fluoro-benzenesulfonyl chloride there was obtained: 4-Fluoro-N-[5-(2-fluoro-phenyl)-6-methyl-pyridin-2-yl]-benzenesulfonamide as a white foam. ISN mass spectrum, m/e: 359 (M−1 calculated for $C_{18}H_{14}F_2N_2O_2S$: 359).

Example 163

In analogy to example 1, on reaction of 5-(2-Fluoro-phenyl)-6-methyl-pyridin-2-ylamine with 4-fluoro-3-trifluoromethyl-benzenesulfonyl chloride there was obtained: 4-Fluoro-N-[5-(2-fluoro-phenyl)-6-methyl-pyridin-2-yl]-3-trifluoromethyl-benzenesulfonamide as a white foam. ISN mass spectrum, m/e: 427.1 (M−1 calculated for $C_{19}H_{13}F_5N_2O_2S$: 427).

Example 164

In analogy to example 1, on reaction of 5-(2,4-bis-trifluoromethyl-phenyl)-pyridin-2-ylamine with 3-chloro-4-fluoro-benzenesulfonyl chloride there was obtained: N-[5-(2,4-Bis-trifluoromethyl-phenyl)-pyridin-2-yl]-3-chloro-4-fluoro-benzenesulfonamide as an off-white foam. ISN mass spectrum, m/e: 496.9 (M−1 calculated for $C_{19}H_{10}ClF_7N_2O_2S$: 497)

Example 165

In analogy to example 1, on reaction of 5-(2-Fluoro-phenyl)-6-methyl-pyridin-2-ylamine with 2,4-dichloro-6-methyl-3-benzenesulfonyl chloride there was obtained: 2,4-Dichloro-N-[5-(2-fluoro-phenyl)-6-methyl-pyridin-2-yl]-6-methyl-benzenesulfonamide as an off-white foam. ISN mass spectrum, m/e: 422.9 (M−1 calculated for $C_{19}H_{15}Cl_2FN_2O_2S$: 423).

Example 166

In analogy to example 1, on reaction of 5-(2-Fluoro-phenyl)-6-methyl-pyridin-2-ylamine with 3-trifluoromethyl-benzenesulfonyl chloride there was obtained: N-[5-(2-Fluoro-phenyl)-6-methyl-pyridin-2-yl]-3-trifluoromethyl-benzenesulfonamide as a light-yellow foam. ISN mass spectrum, m/e: 409.1 (M−1 calculated for $C_{19}H_{14}F_4N_2O_2S$: 409).

Example 167

In analogy to example 1, on reaction of 5-(2-Chloro-phenyl)-3,4-dimethyl-pyridin-2-ylamine with 3-trifluoro-benzenesulfonyl chloride there was obtained: N-[5-(2-Chloro-phenyl)-3,4-dimethyl-pyridin-2-yl]-3-trifluoromethyl-benzenesulfonamide as a yellow amorphous solid. ISN mass spectrum, m/e: 439.1 (M−1 calculated for $C_{20}H_{16}ClF_3N_2O_2S$: 439).
Preparation of the Starting Material:
In analogy to example 1b), on reaction of 5-bromo-3,4-dimethyl-pyridin-2-ylamine with 2-chloro-phenylboronic acid there was obtained: 5-(2-Chloro-phenyl)-3,4-dimethyl-pyridin-2-ylamine a white solid. ISP mass spectrum, m/e: 233 (M+1 calculated for $C_{13}H_{13}ClN_2$: 233).

Example 168

In analogy to example 1, on reaction of 5-(2-Chloro-phenyl)-3,4-dimethyl-pyridin-2-ylamine with 3-chloro-benzenesulfonyl chloride there was obtained: 3-Chloro-N-[5-(2-chloro-phenyl)-3,4-dimethyl-pyridin-2-yl]-benzenesulfonamide as a yellow amorphous solid. ISN mass spectrum, m/e: 405.1 (M−1 calculated for $C_{19}H_{16}Cl_2N_2O_2S$: 405).

Example 169

In analogy to example 1, on reaction of 5-(2-Chloro-phenyl)-3,4-dimethyl-pyridin-2-ylamine with 4-fluoro-benzenesulfonyl chloride there was obtained: N-[5-(2-Chloro-phenyl)-3,4-dimethyl-pyridin-2-yl]-4-fluoro-benzenesulfonamide as a yellow amorphous solid. ISN mass spectrum, m/e: 389 (M−1 calculated for $C_{19}H_{16}ClFN_2O_2S$: 389).

Example 170

In analogy to example 1, on reaction of 2-Methyl-[3,3']bipyridinyl-6-ylamine with 3-trifluoro-benzenesulfonyl chloride there was obtained: N-(2-Methyl-[3,3']bipyridinyl-6-yl)-3-trifluoromethyl-benzenesulfonamide as a light-yellow amorphous solid. ISN mass spectrum, m/e: 392 (M−1 calculated for $C_{18}H_{14}F_3N_3O_2S$: 392).
Preparation of the Starting Material:
In analogy to example 1b), on reaction of 5-bromo-6-methyl-pyridin-2-ylamine with 3-pyridylboronic acid there was obtained: 2-Methyl-[3,3']bipyridinyl-6-ylamine a yellow solid. EI mass spectrum, m/e: 185.2 (M calculated for $C_{11}H_{11}N_3$: 185).

Example 171

In analogy to example 1, on reaction of 5-(2-Chloro-phenyl)-4-methyl-pyridin-2-ylamine with 3-chloro-benzenesulfonyl chloride there was obtained: 3-Chloro-N-[5-(2-chloro-phenyl)-4-methyl-pyridin-2-yl]-benzenesulfonamide as a white solid. ISN mass spectrum, m/e: 391 (M−1 calculated for $C_{18}H_{14}Cl_2N_2O_2S$: 391).
Preparation of the Starting Material:
In analogy to example 1b), on reaction of 5-bromo-4-methyl-pyridin-2-ylamine with 2-chloro-phenylboronic acid there was obtained: 5-(2-Chloro-phenyl)-4-methyl-pyridin- 2-ylamine a yellow solid. EI mass spectrum, m/e: 218.1 (M calculated for $C_{12}H_{11}ClN_2$: 218).

Example 172

In analogy to example 1, on reaction of 5-(2-Chloro-phenyl)-4-methyl-pyridin-2-ylamine with 3-trifluoromethyl-benzenesulfonyl chloride there was obtained: N-[5-(2-Chloro-phenyl)-4-methyl-pyridin-2-yl]-3-trifluoromethyl-benzenesulfonamide as an off-white solid. ISN mass spectrum, m/e: 425.1 (M−1 calculated for $C_{19}H_{14}ClF_3N_2O_2S$: 425).

Example 173

In analogy to example 1, on reaction of 5-(2-Chloro-phenyl)-4-methyl-pyridin-2-ylamine with 2,4-dichloro-6-methyl-benzenesulfonyl chloride there was obtained: 2,4-Dichloro-N-[5-(2-chloro-phenyl)-4-methyl-pyridin-2-yl]-6-methyl-benzenesulfonamide as a white solid. ISN mass spectrum, m/e: 439 (M−1 calculated for $C_{19}H_{15}Cl_3N_2O_2S$: 439).

Example 174

In analogy to example 1, on reaction of 2-Methyl-[3,3']bipyridinyl-6-ylamine with 3-chloro-benzenesulfonyl chloride there was obtained: 3-Chloro-N-(2-methyl-[3,3']bipyridinyl-6-yl)-benzenesulfonamide as a light-brown amorphous solid. ISN mass spectrum, m/e: 358 (M−1 calculated for $C_{17}H_{14}ClN_3O_2S$: 358).

Example 175

In analogy to example 1, on reaction of 5-(4-Fluoro-2-methyl-phenyl)-4-methyl-pyridin-2-ylamine with 3-chloro-benzenesulfonyl chloride there was obtained: 3-Chloro-N-[5-(4-fluoro-2-methyl-phenyl)-4-methyl-pyridin-2-yl]-benzenesulfonamide as a colorless solid. ISN mass spectrum, m/e: 389 (M−1 calculated for $C_{19}H_{16}ClFN_2O_2S$: 389).
Preparation of the Starting Material:

In analogy to example 1b), on reaction of 5-bromo-4-methyl-pyridin-2-ylamine with 2-chloro-phenylboronic acid there was obtained: 5-(4-Fluoro-2-methyl-phenyl)-4-methyl-pyridin-2-ylamine as an amorphous light-yellow solid. ISP mass spectrum, m/e: 217.3 (M+1 calculated for $C_{13}H_{13}FN_2$: 217).

Example 176

In analogy to example 1, on reaction of 5-(4-Fluoro-2-methyl-phenyl)-4-methyl-pyridin-2-ylamine with 3-trifluoromethyl-benzenesulfonyl chloride there was obtained: N-[5-(4-Fluoro-2-methyl-phenyl)-4-methyl-pyridin-2-yl]-3-trifluoromethyl-benzenesulfonamide as a white solid. ISN mass spectrum, m/e: 423 (M−1 calculated for $C_{20}H_{16}F_4N_2O_2S$: 423).

Example 177

In analogy to example 1, on reaction of 5-(4-Fluoro-2-methyl-phenyl)-4-methyl-pyridin-2-ylamine with 2,4-dichloro-6-methyl-trifluoromethyl-benzenesulfonyl chloride there was obtained: 2,4-Dichloro-N-[5-(4-fluoro-2-methyl-phenyl)-4-methyl-pyridin-2-yl]-6-methyl-benzenesulfonamide as a white solid. ISN mass spectrum, m/e: 437.2 (M−1 calculated for $C_{20}H_{17}Cl_2FN_2O_2S$: 437).

Example 178

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 179

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Example 180

Assay Procedures
Transient Expression and Partial Purification:

The cDNA encoding the human 11beta-HSD 1 protein was cloned into the expression vector pcDNA3 (Stratagene). This construct (for details see Alex Odermatt et al.; J Biol. Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phosphate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated with a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.
Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD 1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD 1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there IC50 values, e.g. the concentration at which the production of cortisol was 50% reduced.

In this test preferred compounds as described above have IC50 values below 1000 nM; more preferred compounds have IC50 values below 100 nM. Most preferred compounds have IC50 values below 10 nM.

Cellular Assay

To measure the effect of inhibitors in intact cells HEK293 cells stably expressing human 11beta-HSD 1 (see above) were cultivated in 96 well plates in DMEM. First inhibitors and 60 min later Cortisone was added to the cells. After 60 min of incubation at 37° C. in a 5% CO2 atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound | h 11-beta-HSD 1 IC$_{50}$ (nM) |
| --- | --- |
| Example 2 | 3 |
| Example 110 | 12 |

It is to be understood that the invention is not limited to the particular embodiments of the invention described above, as variations of the particular embodiments may be made and still fall within the scope of the appended claims.

What is claimed is:

1. A compound of the formula (I):

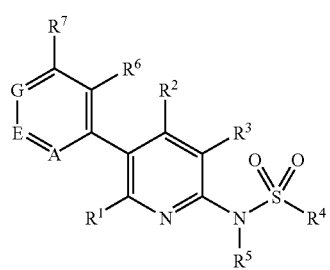

wherein:

$R^1$ is hydrogen, alkyl, cycloalkyl, hydroxy, hydroxyalkyl, alkoxy, alkoxyalkyl, amino or aminoalkyl;

$R^2$ is hydrogen, alkyl or halogen;

$R^3$ is hydrogen, alkyl or halogen;

$R^4$ is phenyl, naphthyl, thiophenyl, pyridyl, quinolyl, piperidyl, morpholyl or thiomorpholyl optionally substituted with one or more substituents independently selected from alkyl, cycloalkyl, halogen, hydroxy, hydroxyalkyl, alkoxy, alkoxyalkyl, hydroxyalkoxy, alkoxyalkoxy, cyano, trifluoromethyl, trifluoromethoxy, aryl, arylalkyl, aryloxy, heterocyclyl, alkylcarbonylamino, alkoxycarbonylalkoxy and alkyl-SO$_2$—;

$R^5$ is hydrogen or alkyl;

$R^6$, $R^7$, $R^8$, $R^9$ and $R^{10}$ are independently selected from hydrogen, alkyl, halogen, cyano, trifluoromethyl, alkoxy and alkyl-SO$_2$—;

A is nitrogen or C—$R^{10}$;

E is nitrogen or C—$R^9$; and

G is nitrogen or C—$R^8$;

wherein not more than one of A, E and G is nitrogen;

or a pharmaceutically acceptable salt or an ester thereof.

2. The compound according to claim 1, wherein $R^1$ is hydrogen.

3. The compound according to claim 1, wherein $R^1$ is alkyl.

4. The compound according to claim 1, wherein $R^2$ is hydrogen.

5. The compound according to claim 1, wherein $R^2$ is alkyl.

6. The compound according to claim 1, wherein $R^3$ is hydrogen.

7. The compound according to claim 1, wherein $R^3$ is alkyl.

8. The compound according to claim 1, wherein $R^5$ is hydrogen.

9. The compound according to claim 1, wherein A is C—$R^{10}$.

10. The compound according to claim 1, wherein E is C—$R^9$.

11. The compound according to claim 1, wherein E is nitrogen.

12. The compound according to claim 1, wherein G is C—$R^8$.

13. The compound according to claim 1, wherein $R^4$ is phenyl optionally substituted with one to three substituents independently selected from alkyl, cycloalkyl, halogen, hydroxy, hydroxyalkyl, alkoxy, alkoxyalkyl, hydroxyalkoxy, alkoxyalkoxy, cyano, trifluoromethyl, trifluoromethoxy, aryl, arylalkyl, aryloxy, heterocyclyl, alkylcarbonylamino, alkoxycarbonylalkoxy and alkyl-SO$_2$—.

14. The compound according to claim 13, wherein $R^4$ is phenyl substituted with one to three substituents independently selected from alkyl, halogen and trifluoromethyl.

15. The compound according to claim 1, wherein $R^6$, $R^7$, $R^8$, $R^9$ and $R^{10}$ are independently selected from hydrogen, alkyl, halogen and trifluoromethyl.

16. The compound according to claim 1, wherein $R^6$ is halogen, alkyl or trifluoromethyl.

17. The compound according to claim 16, wherein $R^6$ is chloro, methyl or trifluoromethyl.

18. The compound according to claim 1 selected from

N-[5-(2-Chloro-phenyl)-pyridin-2-yl]-5-fluoro-2-methyl-benzene sulfonamide;

3-Chloro-N-[5-(2-chloro-phenyl)-pyridin-2-yl]-2-methyl-benzenesulfonamide;

N-[5-(2,4-Dichloro-phenyl)-pyridin-2-yl]-5-fluoro-2-methyl-benzenesulfonamide;

3-Chloro-N-[5-(2,4-dichloro-phenyl)-pyridin-2-yl]-2-methyl-benzenesulfonamide;

3-Chloro-N-[5-(2-chloro-phenyl)-6-methyl-pyridin-2-yl]-2-methyl-benzenesulfonamide;
Biphenyl-4-sulfonic acid [5-(2-chloro-phenyl)-6-methyl-pyridin-2-yl]-amide;
3-Chloro-N-[5-(2-chloro-4-fluoro-phenyl)-pyridin-2-yl]-2-methyl-benzenesulfonamide;
3-Chloro-N-[5-(3-fluoro-phenyl)-pyridin-2-yl]-2-methyl-benzenesulfonamide;
3-Chloro-N-[5-(2,4-difluoro-phenyl)-pyridin-2-yl]-2-methyl-benzenesulfonamide;
N-[5-(2,4-Difluoro-phenyl)-pyridin-2-yl]-5-fluoro-2-methyl-benzene sulfonamide;
3-Chloro-N-[5-(4-methoxy-phenyl)-pyridin-2-yl]-2-methyl-benzenesulfonamide;
3-Chloro-N-[5-(4-fluoro-phenyl)-pyridin-2-yl]-2-methyl-benzenesulfonamide;
5-Fluoro-N-[5-(4-fluoro-phenyl)-pyridin-2-yl]-2-methyl-benzene sulfonamide;
5-Fluoro-N-[5-(2-methoxy-phenyl)-pyridin-2-yl]-2-methyl-benzenesulfonamide;
3-Chloro-N-[5-(2-fluoro-phenyl)-pyridin-2-yl]-2-methyl-benzenesulfonamide;
5-Fluoro-N-[5-(2-fluoro-phenyl)-pyridin-2-yl]-2-methyl-benzene sulfonamide;
2,4-Dichloro-N-[5-(2-chloro-phenyl)-pyridin-2-yl]-6-methyl-benzenesulfonamide;
N-[5-(2-Chloro-phenyl)-pyridin-2-yl]-2,5-difluoro-benzenesulfonamide;
3-Chloro-N-[5-(4-methanesulfonyl-phenyl)-pyridin-2-yl]-2-methyl-benzenesulfonamide;
3-Chloro-N-[5-(4-fluoro-phenyl)-6-methyl-pyridin-2-yl]-2-methyl-benzenesulfonamide;
5-Fluoro-N-[5-(4-fluoro-phenyl)-6-methyl-pyridin-2-yl]-2-methyl-benzenesulfonamide;
3-Chloro-N-[5-(3-fluoro-phenyl)-6-methyl-pyridin-2-yl]-2-methyl-benzenesulfonamide;
5-Fluoro-N-[5-(3-fluoro-phenyl)-6-methyl-pyridin-2-yl]-2-methyl-benzenesulfonamide;
N-[5-(2,4-Dichloro-phenyl)-pyridin-2-yl]-3,4-dimethoxy-benzenesulfonamide;
3,4-Dichloro-N-[5-(2,4-dichloro-phenyl)-pyridin-2-yl]-benzenesulfonamide;
N-[5-(2,3-Dichloro-phenyl)-pyridin-2-yl]-2,5-difluoro-benzenesulfonamide;
3-Chloro-N-[5-(2,3-dichloro-phenyl)-pyridin-2-yl]-2-methyl-benzenesulfonamide;
3,4-Dichloro-N-[5-(2-chloro-phenyl)-pyridin-2-yl]-benzenesulfonamide;
N-[5-(2-Chloro-phenyl)-pyridin-2-yl]-3,4-dimethoxy-benzenesulfonamide;
3-Chloro-N-[5-(2-chloro-phenyl)-pyridin-2-yl]-4-methyl-benzenesulfonamide;
5-Fluoro-N-[5-(4-fluoro-2-methyl-phenyl)-pyridin-2-yl]-2-methyl-benzenesulfonamide;
3-Chloro-N-[5-(4-fluoro-2-methyl-phenyl)-pyridin-2-yl]-2-methyl-benzenesulfonamide;
3-Chloro-N-[5-(2-chloro-phenyl)-pyridin-2-yl]-4-methoxy-benzenesulfonamide;
4,5-Dichloro-N-[5-(2-chloro-phenyl)-pyridin-2-yl]-2-fluoro-benzenesulfonamide;
3-Chloro-N-[5-(2,4-dichloro-phenyl)-pyridin-2-yl]-4-methoxy-benzenesulfonamide;
3-Chloro-N-[5-(2,4-dichloro-phenyl)-pyridin-2-yl]-4-methyl-benzenesulfonamide;
Piperidine-1-sulfonic acid [5-(2,4-dichloro-phenyl)-pyridin-2-yl]-amide;
N-[5-(2,3-Dichloro-phenyl)-pyridin-2-yl]-2-trifluoromethyl-benzenesulfonamide;
N-[5-(2,3-Dichloro-phenyl)-pyridin-2-yl]-4-fluoro-benzenesulfonamide;
N-[5-(2,5-Dichloro-phenyl)-pyridin-2-yl]-2,5-difluoro-benzenesulfonamide;
N-[5-(2,5-Dichloro-phenyl)-pyridin-2-yl]-5-fluoro-2-methyl-benzenesulfonamide;
3-Chloro-N-[5-(2,5-dichloro-phenyl)-pyridin-2-yl]-2-methyl-benzenesulfonamide;
5-Fluoro-N-[5-(2-fluoro-5-trifluoromethyl-phenyl)-pyridin-2-yl]-2-methyl-benzenesulfonamide;
3-Chloro-N-[5-(2-fluoro-5-trifluoromethyl-phenyl)-pyridin-2-yl]-2-methyl-benzenesulfonamide;
3-Chloro-2-methyl-N-[5-(2-trifluoromethyl-phenyl)-pyridin-2-yl]-benzenesulfonamide;
3-Chloro-4-methyl-N-[5-(2-trifluoromethyl-phenyl)-pyridin-2-yl]-benzenesulfonamide;
5-Chloro-N-[5-(2,4-dichloro-phenyl)-pyridin-2-yl]-2-methoxy-benzenesulfonamide;
N-{2-Chloro-4-[5-(2,4-dichloro-phenyl)-pyridin-2-ylsulfamoyl]-phenyl}-acetamide;
N-[5-(2,4-Dichloro-phenyl)-pyridin-2-yl]-4-trifluoromethyl-benzenesulfonamide;
N-[5-(2,4-Dichloro-phenyl)-pyridin-2-yl]-4-methylsulfonyl-benzenesulfonamide;
3-Chloro-N-[5-(2,3-difluoro-phenyl)-pyridin-2-yl]-4-methyl-benzenesulfonamide;
N-[5-(2,3-Difluoro-phenyl)-pyridin-2-yl]-5-fluoro-2-methyl-benzenesulfonamide;
N-[5-(2,4-Bis-trifluoromethyl-phenyl)-pyridin-2-yl]-3-chloro-2-methyl-benzenesulfonamide;
N-[5-(2,4-Bis-trifluoromethyl-phenyl)-pyridin-2-yl]-3-chloro-4-methyl-benzenesulfonamide;
3-Chloro-N-[5-(2,3-difluoro-phenyl)-pyridin-2-yl]-2-methyl-benzenesulfonamide;
Piperidine-1-sulfonic acid [5-(2,3-dichloro-phenyl)-pyridin-2-yl]-amide;
5-Chloro-N-[5-(4-fluoro-phenyl)-6-methyl-pyridin-2-yl]-2-methoxy-benzenesulfonamide;
N-{2-Chloro-4-[5-(4-fluoro-phenyl)-6-methyl-pyridin-2-ylsulfamoyl]-phenyl}-acetamide;
N-[5-(4-Fluoro-phenyl)-6-methyl-pyridin-2-yl]-4-trifluoromethyl-benzenesulfonamide;
N-[5-(4-Fluoro-phenyl)-6-methyl-pyridin-2-yl]-4-methanesulfonyl-benzenesulfonamide;
{4-[5-(2,3-Dichloro-phenyl)-pyridin-2-ylsulfamoyl]-phenoxy}-acetic acid methyl ester;
N-[5-(4-Fluoro-phenyl)-6-methyl-pyridin-2-yl]-4-trifluoromethoxy-benzenesulfonamide;
3-Chloro-N-[5-(4-fluoro-phenyl)-6-methyl-pyridin-2-yl]-4-methoxy-benzenesulfonamide;
4-Chloro-N-[5-(4-fluoro-phenyl)-6-methyl-pyridin-2-yl]-2,5-dimethyl-benzenesulfonamide;
N-[5-(2,3-Dichloro-phenyl)-pyridin-2-yl]-4-(2-hydroxy-ethoxy)-benzenesulfonamide;
N-[5-(2-Chloro-phenyl)-6-methyl-pyridin-2-yl]-4-fluoro-benzenesulfonamide;
3-Chloro-N-[5-(2-chloro-phenyl)-6-methyl-pyridin-2-yl]-4-methyl-benzenesulfonamide;
4-Chloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-6-methyl-benzenesulfonamide;
Piperidine-1-sulfonic acid [5-(2-chloro-phenyl)-6-methyl-pyridin-2-yl]-amide;

N-[5-(2,4-Dichloro-phenyl)-pyridin-2-yl]-4-fluoro-benzenesulfonamide;
4-Chloro-N-[5-(2,4-dichloro-phenyl)-pyridin-2-yl]-2,5-dimethyl-benzenesulfonamide;
N-[5-(2,4-Dichloro-phenyl)-pyridin-2-yl]-2,4-difluoro-benzenesulfonamide;
2,4-Dichloro-N-[5-(2,4-dichloro-phenyl)-pyridin-2-yl]-5-methyl-benzenesulfonamide;
N-[5-(2,3-Dichloro-phenyl)-pyridin-2-yl]-3-trifluoromethyl-benzenesulfonamide
4-Fluoro-N-[5-(4-fluoro-2-methyl-phenyl)-6-methyl-pyridin-2-yl]-benzenesulfonamide;
3-Chloro-N-[5-(4-fluoro-2-methyl-phenyl)-6-methyl-pyridin-2-yl]-2-methyl-benzenesulfonamide;
5-Fluoro-N-[5-(4-fluoro-2-methyl-phenyl)-6-methyl-pyridin-2-yl]-2-methyl-benzenesulfonamide;
3-Chloro-N-[5-(2,3-dichloro-phenyl)-pyridin-2-yl]-4-methyl-benzenesulfonamide;
N-[5-(2,3-Dichloro-phenyl)-pyridin-2-yl]-4-trifluoromethyl-benzenesulfonamide;
3-Chloro-N-[5-(4-fluoro-2-methyl-phenyl)-pyridin-2-yl]-4-methyl-benzenesulfonamide;
N-[5-(4-Fluoro-2-methyl-phenyl)-pyridin-2-yl]-3-trifluoromethyl-benzenesulfonamide;
N-[5-(4-Fluoro-2-methyl-phenyl)-pyridin-2-yl]-4-trifluoromethyl-benzenesulfonamide;
N-[5-(2-Chloro-phenyl)-pyridin-2-yl]-3-trifluoromethyl-benzenesulfonamide;
N-[5-(2-Chloro-phenyl)-pyridin-2-yl]-4-ethyl-benzenesulfonamide;
3-Chloro-N-[5-(2-chloro-phenyl)-pyridin-2-yl]-benzenesulfonamide;
3-Chloro-N-[5-(2,4-dichloro-phenyl)-pyridin-2-yl]-4-fluoro-benzenesulfonamide;
N-[5-(2,4-Dichloro-phenyl)-pyridin-2-yl]-4-ethyl-benzenesulfonamide;
N-[5-(2,4-Dichloro-phenyl)-pyridin-2-yl]-3-trifluoromethyl-benzenesulfonamide;
N-[5-(2-Chloro-phenyl)-6-methyl-pyridin-2-yl]-3-trifluoromethyl-benzenesulfonamide;
N-[5-(2-Chloro-phenyl)-6-methyl-pyridin-2-yl]-4-trifluoromethoxy-benzenesulfonamide;
N-[5-(2-Chloro-phenyl)-pyridin-2-yl]-4-fluoro-benzenesulfonamide;
N-[5-(2-Chloro-phenyl)-pyridin-2-yl]-2,4-difluoro-benzenesulfonamide;
4-Chloro-N-[5-(2-chloro-phenyl)-pyridin-2-yl]-2,5-dimethyl-benzenesulfonamide;
4-Chloro-N-[5-(2-chloro-phenyl)-6-methyl-pyridin-2-yl]-2,5-dimethyl-benzenesulfonamide;
N-[5-(2-Chloro-phenyl)-6-methyl-pyridin-2-yl]-2,4-difluoro-benzenesulfonamide;
3,5-Dichloro-N-[5-(2-chloro-phenyl)-6-methyl-pyridin-2-yl]-benzenesulfonamide;
N-[5-(2,4-Dichloro-phenyl)-6-methyl-pyridin-2-yl]-3-trifluoromethyl-benzenesulfonamide;
N-[5-(2,4-Dichloro-phenyl)-6-methyl-pyridin-2-yl]-4-fluoro-benzenesulfonamide;
N-[5-(2,4-Dichloro-phenyl)-6-methyl-pyridin-2-yl]-2,4-difluoro-benzenesulfonamide;
4-Chloro-N-[5-(2,4-dichloro-phenyl)-6-methyl-pyridin-2-yl]-2,5-dimethyl-benzenesulfonamide;
2,4-Dichloro-N-[5-(2,4-dichloro-phenyl)-pyridin-2-yl]-6-methyl-benzenesulfonamide;
3-Chloro-N-[5-(2,4-dichloro-phenyl)-pyridin-2-yl]-benzenesulfonamide;
4-Chloro-N-[5-(2,4-dichloro-phenyl)-pyridin-2-yl]-benzenesulfonamide;
N-[5-(2-Chloro-phenyl)-6-methyl-pyridin-2-yl]-3-fluoro-benzenesulfonamide;
3-Chloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-5-methyl-benzenesulfonamide;
N-[5-(4-Fluoro-2-methyl-phenyl)-6-methyl-pyridin-2-yl]-3-trifluoromethyl-benzenesulfonamide;
2,4-Dichloro-N-[5-(4-fluoro-2-methyl-phenyl)-6-methyl-pyridin-2-yl]-6-methyl-benzenesulfonamide;
3-Chloro-N-[5-(4-fluoro-2-methyl-phenyl)-6-methyl-pyridin-2-yl]-benzenesulfonamide;
4-Chloro-N-[5-(4-fluoro-2-methyl-phenyl)-6-methyl-pyridin-2-yl]-benzenesulfonamide;
N-[5-(4-Fluoro-2-methyl-phenyl)-6-methyl-pyridin-2-yl]-4-trifluoromethoxy-benzenesulfonamide;
N-[5-(4-Fluoro-2-methyl-phenyl)-6-methyl-pyridin-2-yl]-3-methyl-benzenesulfonamide;
2-Chloro-N-[5-(4-fluoro-2-methyl-phenyl)-6-methyl-pyridin-2-yl]-5-trifluoromethyl-benzenesulfonamide;
4-Fluoro-N-[5-(4-fluoro-2-methyl-phenyl)-6-methyl-pyridin-2-yl]-3-trifluoromethyl-benzenesulfonamide;
N-[5-(2-Chloro-phenyl)-6-methyl-pyridin-2-yl]-3-methyl-benzenesulfonamide;
3-Chloro-N-[5-(2-chloro-phenyl)-6-methyl-pyridin-2-yl]-4-fluoro-benzenesulfonamide;
2-Chloro-N-[5-(2-chloro-phenyl)-6-methyl-pyridin-2-yl]-5-trifluoromethyl-benzenesulfonamide;
N-[5-(2-Chloro-phenyl)-6-methyl-pyridin-2-yl]-4-fluoro-3-trifluoromethyl-benzenesulfonamide;
N-[5-(2,3-Dichloro-phenyl)-pyridin-2-yl]-3-fluoro-4-methyl-benzenesulfonamide;
N-[5-(2,3-Dichloro-phenyl)-pyridin-2-yl]-3,5-dimethyl-benzenesulfonamide;
N-[5-(5-Fluoro-2-methyl-phenyl)-pyridin-2-yl]-3-trifluoromethyl-benzenesulfonamide;
4-Fluoro-N-[5-(5-fluoro-2-methyl-phenyl)-pyridin-2-yl]-benzenesulfonamide;
3-Chloro-N-[5-(5-fluoro-2-methyl-phenyl)-pyridin-2-yl]-2-methyl-benzenesulfonamide;
N-[5-(5-Chloro-2-methyl-phenyl)-pyridin-2-yl]-3-trifluoromethyl-benzenesulfonamide;
N-[5-(5-Chloro-2-methyl-phenyl)-pyridin-2-yl]-4-fluoro-benzenesulfonamide;
3-Chloro-N-[5-(5-chloro-2-methyl-phenyl)-pyridin-2-yl]-2-methyl-benzenesulfonamide;
3-Chloro-N-[5-(6-chloro-2-fluoro-3-methyl-phenyl)-pyridin-2-yl]-2-methyl-benzenesulfonamide;
N-[5-(6-Chloro-2-fluoro-3-methyl-phenyl)-pyridin-2-yl]-3-trifluoromethyl-benzenesulfonamide;
N-[5-(6-Chloro-2-fluoro-3-methyl-phenyl)-pyridin-2-yl]-4-fluoro-benzenesulfonamide;
N-[5-(5-Chloro-2-methyl-phenyl)-6-methyl-pyridin-2-yl]-3-trifluoromethyl-benzenesulfonamide;
N-[5-(5-Chloro-2-methyl-phenyl)-6-methyl-pyridin-2-yl]-4-fluoro-benzenesulfonamide;
3-Chloro-N-[5-(5-chloro-2-methyl-phenyl)-6-methyl-pyridin-2-yl]-2-methyl-benzenesulfonamide;
N-[5-(6-Chloro-2-fluoro-3-methyl-phenyl)-6-methyl-pyridin-2-yl]-3-trifluoromethyl-benzenesulfonamide;
N-[5-(6-Chloro-2-fluoro-3-methyl-phenyl)-6-methyl-pyridin-2-yl]-4-fluoro-benzenesulfonamide;

4-Chloro-N-[5-(4-fluoro-2-methyl-phenyl)-pyridin-2-yl]-benzenesulfonamide;
3-Chloro-N-[5-(4-fluoro-2-methyl-phenyl)-pyridin-2-yl]-benzenesulfonamide;
2,4-Dichloro-N-[5-(4-fluoro-2-methyl-phenyl)-pyridin-2-yl]-6-methyl-benzenesulfonamide;
3-Chloro-N-[5-(2,5-dichloro-phenyl)-6-methyl-pyridin-2-yl]-benzenesulfonamide;
N-[5-(2,5-Dichloro-phenyl)-6-methyl-pyridin-2-yl]-4-fluoro-benzenesulfonamide;
N-[5-(5-Fluoro-2-methyl-phenyl)-6-methyl-pyridin-2-yl]-3-trifluoromethyl-benzenesulfonamide;
4-Fluoro-N-[5-(5-fluoro-2-methyl-phenyl)-6-methyl-pyridin-2-yl]-benzenesulfonamide;
3-Chloro-N-[5-(5-fluoro-2-methyl-phenyl)-6-methyl-pyridin-2-yl]-benzenesulfonamide;
N-[5-(2,5-Dichloro-phenyl)-6-methyl-pyridin-2-yl]-3-trifluoromethyl-benzenesulfonamide;
N-[5-(2-Chloro-4-fluoro-phenyl)-6-methyl-pyridin-2-yl]-3-trifluoromethyl-benzenesulfonamide;
N-[5-(2-Chloro-4-fluoro-phenyl)-6-methyl-pyridin-2-yl]-4-fluoro-benzenesulfonamide;
3-Chloro-N-[5-(2-chloro-4-fluoro-phenyl)-6-methyl-pyridin-2-yl]-benzenesulfonamide;
N-[5-(2,3-Dichloro-phenyl)-6-methyl-pyridin-2-yl]-3-trifluoromethyl-benzenesulfonamide;
N-[5-(2,3-Dichloro-phenyl)-6-methyl-pyridin-2-yl]-4-fluoro-benzenesulfonamide;
3-Chloro-N-[5-(2,3-dichloro-phenyl)-6-methyl-pyridin-2-yl]-benzenesulfonamide;
2,4-Dichloro-N-[5-(2,3-dichloro-phenyl)-6-methyl-pyridin-2-yl]-6-methyl-benzenesulfonamide;
N-[5-(2,3-Dichloro-phenyl)-6-methyl-pyridin-2-yl]-3-methyl-benzenesulfonamide;
2,4-Dichloro-N-[5-(2,5-dichloro-phenyl)-6-methyl-pyridin-2-yl]-6-methyl-benzenesulfonamide;
N-[5-(2-Chloro-4-fluoro-phenyl)-6-methyl-pyridin-2-yl]-3-methyl-benzenesulfonamide;
2,4-Dichloro-N-[5-(2-chloro-4-fluoro-phenyl)-6-methyl-pyridin-2-yl]-6-methyl-benzenesulfonamide;
N-[5-(2,4-Bis-trifluoromethyl-phenyl)-pyridin-2-yl]-3-chloro-benzenesulfonamide;
N-[5-(2,4-Bis-trifluoromethyl-phenyl)-pyridin-2-yl]-3-methyl-benzenesulfonamide;
N-[5-(2,4-Bis-trifluoromethyl-phenyl)-pyridin-2-yl]-4-fluoro-benzenesulfonamide;
N-[5-(2,3-Dichloro-phenyl)-6-methyl-pyridin-2-yl]-4-fluoro-3-trifluoromethyl-benzenesulfonamide;
3-Chloro-N-[5-(2,3-dichloro-phenyl)-6-methyl-pyridin-2-yl]-4-fluoro-benzenesulfonamide;
3-Chloro-N-[5-(2-fluoro-phenyl)-6-methyl-pyridin-2-yl]-benzenesulfonamide;
4-Fluoro-N-[5-(2-fluoro-phenyl)-6-methyl-pyridin-2-yl]-benzenesulfonamide;
4-Fluoro-N-[5-(2-fluoro-phenyl)-6-methyl-pyridin-2-yl]-3-trifluoromethyl-benzenesulfonamide;
N-[5-(2,4-Bis-trifluoromethyl-phenyl)-pyridin-2-yl]-3-chloro-4-fluoro-benzenesulfonamide;
2,4-Dichloro-N-[5-(2-fluoro-phenyl)-6-methyl-pyridin-2-yl]-6-methyl-benzenesulfonamide;
N-[5-(2-Fluoro-phenyl)-6-methyl-pyridin-2-yl]-3-trifluoromethyl-benzenesulfonamide;
N-[5-(2-Chloro-phenyl)-3,4-dimethyl-pyridin-2-yl]-3-trifluoromethyl-benzenesulfonamide;
3-Chloro-N-[5-(2-chloro-phenyl)-3,4-dimethyl-pyridin-2-yl]-benzenesulfonamide;
N-[5-(2-Chloro-phenyl)-3,4-dimethyl-pyridin-2-yl]-4-fluoro-benzenesulfonamide;
N-(2-Methyl-[3,3']bipyridinyl-6-yl)-3-trifluoromethyl-benzenesulfonamide;
3-Chloro-N-[5-(2-chloro-phenyl)-4-methyl-pyridin-2-yl]-benzenesulfonamide;
N-[5-(2-Chloro-phenyl)-4-methyl-pyridin-2-yl]-3-trifluoromethyl-benzenesulfonamide;
2,4-Dichloro-N-[5-(2-chloro-phenyl)-4-methyl-pyridin-2-yl]-6-methyl-benzenesulfonamide;
3-Chloro-N-(2-methyl-[3,3']bipyridinyl-6-yl)-benzenesulfonamide;
3-Chloro-N-[5-(4-fluoro-2-methyl-phenyl)-4-methyl-pyridin-2-yl]-benzenesulfonamide;
N-[5-(4-Fluoro-2-methyl-phenyl)-4-methyl-pyridin-2-yl]-3-trifluoromethyl-benzenesulfonamide; and
2,4-Dichloro-N-[5-(4-fluoro-2-methyl-phenyl)-4-methyl-pyridin-2-yl]-6-methyl-benzenesulfonamide.

19. The compound according to claim 1 selected from
N-[5-(2-Chloro-phenyl)-pyridin-2-yl]-5-fluoro-2-methyl-benzenesulfonamide;
3-Chloro-N-[5-(2-chloro-phenyl)-pyridin-2-yl]-2-methyl-benzenesulfonamide;
3-Chloro-N-[5-(2,4-dichloro-phenyl)-pyridin-2-yl]-2-methyl-benzenesulfonamide;
3-Chloro-N-[5-(2-chloro-phenyl)-6-methyl-pyridin-2-yl]-2-methyl-benzenesulfonamide;
4,5-Dichloro-N-[5-(2-chloro-phenyl)-pyridin-2-yl]-2-fluoro-benzenesulfonamide;
3-Chloro-N-[5-(2,4-dichloro-phenyl)-pyridin-2-yl]-4-methyl-benzenesulfonamide;
Piperidine-1-sulfonic acid [5-(2,4-dichloro-phenyl)-pyridin-2-yl]-amide;
N-[5-(2,3-Dichloro-phenyl)-pyridin-2-yl]-4-fluoro-benzenesulfonamide;
3-Chloro-N-[5-(2-chloro-phenyl)-6-methyl-pyridin-2-yl]-4-methyl-benzenesulfonamide;
4-Chloro-N-[5-(2-chloro-phenyl)-6-methyl-pyridin-2-yl]-benzenesulfonamide;
2,4-Dichloro-N-[5-(2-chloro-phenyl)-6-methyl-pyridin-2-yl]-6-methyl-benzenesulfonamide;
N-[5-(2,4-Dichloro-phenyl)-pyridin-2-yl]-4-fluoro-benzenesulfonamide;
N-[5-(2,4-Dichloro-phenyl)-pyridin-2-yl]-2,4-difluoro-benzenesulfonamide;
3-Chloro-N-[5-(4-fluoro-2-methyl-phenyl)-6-methyl-pyridin-2-yl]-2-methyl-benzenesulfonamide;
3-Chloro-N-[5-(2,3-dichloro-phenyl)-pyridin-2-yl]-4-methyl-benzenesulfonamide;
3-Chloro-N-[5-(4-fluoro-2-methyl-phenyl)-pyridin-2-yl]-4-methyl-benzenesulfonamide;
N-[5-(4-Fluoro-2-methyl-phenyl)-pyridin-2-yl]-3-trifluoromethyl-benzenesulfonamide;
N-[5-(2,4-Dichloro-phenyl)-pyridin-2-yl]-3-trifluoromethyl-benzenesulfonamide;
N-[5-(2-Chloro-phenyl)-6-methyl-pyridin-2-yl]-3-trifluoromethyl-benzenesulfonamide;
N-[5-(2-Chloro-phenyl)-pyridin-2-yl]-4-fluoro-benzenesulfonamide;
N-[5-(2-Chloro-phenyl)-6-methyl-pyridin-2-yl]-2,4-difluoro-benzenesulfonamide;
N-[5-(2,4-Dichloro-phenyl)-6-methyl-pyridin-2-yl]-2,4-difluoro-benzenesulfonamide;
2,4-Dichloro-N-[5-(2,4-dichloro-phenyl)-pyridin-2-yl]-6-methyl-benzenesulfonamide;
2,4-Dichloro-N-[5-(2-chloro-phenyl)-6-methyl-pyridin-2-yl]-benzenesulfonamide;

N-[5-(4-Fluoro-2-methyl-phenyl)-6-methyl-pyridin-2-yl]-3-trifluoromethyl-benzenesulfonamide;
3-Chloro-N-[5-(4-fluoro-2-methyl-phenyl)-6-methyl-pyridin-2-yl]-benzenesulfonamide;
N-[5-(4-Fluoro-2-methyl-phenyl)-6-methyl-pyridin-2-yl]-3-methyl-benzenesulfonamide;
N-[5-(5-Fluoro-2-methyl-phenyl)-pyridin-2-yl]-3-trifluoromethyl-benzenesulfonamide;
N-[5-(5-Chloro-2-methyl-phenyl)-pyridin-2-yl]-3-trifluoromethyl-benzenesulfonamide;
N-[5-(6-Chloro-2-fluoro-3-methyl-phenyl)-pyridin-2-yl]-4-fluoro-benzenesulfonamide;
3-Chloro-N-[5-(4-fluoro-2-methyl-phenyl)-pyridin-2-yl]-benzenesulfonamide;
2,4-Dichloro-N-[5-(4-fluoro-2-methyl-phenyl)-pyridin-2-yl]-6-methyl-benzenesulfonamide;
4-Fluoro-N-[5-(5-fluoro-2-methyl-phenyl)-6-methyl-pyridin-2-yl]-benzenesulfonamide;
N-[5-(2-Chloro-4-fluoro-phenyl)-6-methyl-pyridin-2-yl]-3-trifluoromethyl-benzenesulfonamide;
2,4-Dichloro-N-[5-(2,3-dichloro-phenyl)-6-methyl-pyridin-2-yl]-6-methyl-benzenesulfonamide;
2,4-Dichloro-N-[5-(2-chloro-4-fluoro-phenyl)-6-methyl-pyridin-2-yl]-6-methyl-benzenesulfonamide;
N-[5-(2,4-Bis-trifluoromethyl-phenyl)-pyridin-2-yl]-3-chloro-benzenesulfonamide;
3-Chloro-N-[5-(2-chloro-phenyl)-4-methyl-pyridin-2-yl]-benzenesulfonamide;
N-[5-(2-Chloro-phenyl)-4-methyl-pyridin-2-yl]-3-trifluoromethyl-benzenesulfonamide;
3-Chloro-N-[5-(4-fluoro-2-methyl-phenyl)-4-methyl-pyridin-2-yl]-benzenesulfonamide;
N-[5-(4-Fluoro-2-methyl-phenyl)-4-methyl-pyridin-2-yl]-3-trifluoromethyl-benzenesulfonamide; and
2,4-Dichloro-N-[5-(4-fluoro-2-methyl-phenyl)-4-methyl-pyridin-2-yl]-6-methyl-benzenesulfonamide.

20. A process for the preparation of a compound according to claim 1 comprising of the step of reacting a compound according to formula (II):

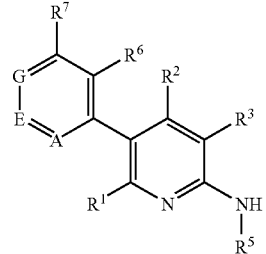

(II)

in the presence of a compound according to formula

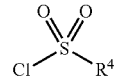

wherein $R^1$ to $R^7$, A, E and G are defined as in claim 1.

21. A pharmaceutical composition comprising a therapeutically effective amount of a compound according to claim 1 and a therapeutically inert carrier.

* * * * *